(12) United States Patent
Sekiguchi

(10) Patent No.: US 7,968,615 B2
(45) Date of Patent: Jun. 28, 2011

(54) POLYMERIZABLE MONOMER, POLYMERIZABLE COMPOSITION AND DENTAL MATERIAL

(75) Inventor: Takahiro Sekiguchi, Kurashiki (JP)

(73) Assignee: Kuraray Medical Inc., Kurashiki-shi (JP)

(*) Notice: Subject to any disclaimer, the term of this patent is extended or adjusted under 35 U.S.C. 154(b) by 75 days.

(21) Appl. No.: 12/532,289

(22) PCT Filed: Mar. 6, 2008

(86) PCT No.: PCT/JP2008/054087
§ 371 (c)(1),
(2), (4) Date: Sep. 21, 2009

(87) PCT Pub. No.: WO2008/114621
PCT Pub. Date: Sep. 25, 2008

(65) Prior Publication Data
US 2010/0056665 A1 Mar. 4, 2010

(30) Foreign Application Priority Data
Mar. 20, 2007 (JP) .............................. 2007-073603

(51) Int. Cl.
*A61K 6/08* (2006.01)
*C08L 33/24* (2006.01)
*C08L 33/14* (2006.01)
*C08F 20/58* (2006.01)
*C08F 20/26* (2006.01)

(52) U.S. Cl. ........ 523/116; 525/218; 525/223; 526/304; 526/320

(58) Field of Classification Search .................. 523/116; 526/320, 304; 525/223, 218
See application file for complete search history.

(56) References Cited

U.S. PATENT DOCUMENTS

| | | | |
|---|---|---|---|
| 4,719,297 A | 1/1988 | Henne et al. | |
| 5,204,383 A | 4/1993 | Manabe et al. | |
| 5,399,770 A | 3/1995 | Leppard et al. | |
| 5,539,017 A | 7/1996 | Rheinberger et al. | |
| 5,648,441 A | 7/1997 | Keller et al. | |
| 5,942,290 A | 8/1999 | Leppard et al. | |
| 6,107,358 A | 8/2000 | Harada et al. | |
| 2004/0005524 A1 | 1/2004 | Oxman et al. | |
| 2005/0042363 A1 | 2/2005 | Kukhtin et al. | |
| 2005/0256221 A1 | 11/2005 | Zeng et al. | |

FOREIGN PATENT DOCUMENTS

| | | |
|---|---|---|
| EP | 0 009 348 | 7/1983 |
| JP | 57 197289 | 12/1982 |
| JP | 64 90277 | 4/1989 |
| JP | 3 279307 | 12/1991 |
| JP | 5 345790 | 12/1993 |
| JP | 6 234939 | 8/1994 |
| JP | 7 258018 | 10/1995 |
| JP | 9 3109 | 1/1997 |
| JP | 10 95788 | 4/1998 |
| JP | 10 245525 | 9/1998 |
| JP | 10 251310 | 9/1998 |
| JP | 2000 53519 | 2/2000 |
| JP | 2000 159621 | 6/2000 |
| JP | 2003 96122 | 4/2003 |
| JP | 2004 43427 | 2/2004 |
| JP | 2004 91949 | 3/2004 |
| JP | 2005 171213 | 6/2005 |
| JP | 2005 531632 | 10/2005 |
| WO | 2004 047773 | 6/2004 |

OTHER PUBLICATIONS

Obata, Makoto et al., "Chirality Induction in Cyclopolymerization. 8. Cyclocopolymerization of 1,2:5,6-Di-*O*-isopropylidene- 3,4-di-*O*-methacryloyl-D-mannitol with Styrene", Macromolecules, vol. 30, No. 3, pp. 348-353, (1997).
Lou, Xia et al., "Hydrophilic Sponges Based on 2-Hydroxyethyl Methacrylate. IV. Novel Synthetic Routes to Hydroxyl-Containing Crosslinking Agents and Their Effect on the Mechanical Strength of Sponges", International Journal of Polymeric Materials, vol. 37, No. 1-2, pp. 1-14, (Jun. 12, 1997).
Horak, D. et al., "A novel hydrophilic crosslinker in preparation of hydrophilic sorbents", Reactive & Functional Polymers, vol. 32, pp. 277-280, (May 28, 1997).
U.S. Appl. No. 12/523,554, filed Jul. 17, 2009, Hinamoto, et al.
U.S. Appl. No. 12/523,546, filed Jul. 17, 2009, Ishino, et al.
U.S. Appl. No. 12/523,538, filed Jul. 17, 2009, Ishino, et al.
U.S. Appl. No. 12/523,591, filed Jul. 17, 2009, Ishino, et al.
U.S. Appl. No. 12/532,289, filed Sep. 21, 2009, Sekiguchi.

*Primary Examiner* — Mark Eashoo
*Assistant Examiner* — David Karst
(74) *Attorney, Agent, or Firm* — Oblon, Spivak, McClelland, Maier & Neustadt, L.L.P.

(57) ABSTRACT

The present invention provides a polymerizable composition that imparts excellent adhesive properties with respect to tooth structure (particularly dentin) when applied as a dental material, and provides a polymerizable monomer that is used as a component of the polymerizable composition. The present invention is a compound (A) that is a compound represented by the following formula (1): where G indicates a polymerizable group, m indicates an integer of 2 or more, n indicates an integer of 1 or more, and the sequence order of m units having a polymerizable group and n units having a hydroxyl group is arbitrary. The present invention also is a polymerizable composition containing the compound (A).

19 Claims, No Drawings

POLYMERIZABLE MONOMER, POLYMERIZABLE COMPOSITION AND DENTAL MATERIAL

TECHNICAL FIELD

The present invention relates to polymerizable monomers that are mainly used for dental materials and that has a plurality of polymerizable groups and hydroxyl groups, and to polymerizable compositions that contain the polymerizable monomers. The present invention also relates to dental materials using the polymerizable compositions, such as dental primers, bonding materials, cements, and composite resins.

BACKGROUND ART

When a lost part of a tooth is filled or covered with a restorative material, generally a dental adhesive is used. A known dental adhesive is one containing a polymerizable monomer having a polymerizable group and a hydroxyl group.

For example, WO 2004/047773 describes a dental adhesive composition characterized by containing a polyfunctional polymerizable monomer that is an ester compound of polyhydric alcohol having 3 to 6 carbon atoms and a plurality of (meth)acrylic acids and that has one to two hydroxyl groups, a monofunctional (meth)acrylate having no hydroxyl group in the molecule, a polymerizable monomer having an acidic group in the molecule, an organoboron compound as a curing agent, and a filler. This describes that the addition of a small amount of the above polyfunctional polymerizable monomer to the composition can improve the cure rate considerably almost without affecting the adhesive properties of the composition, physical properties of the cured product, or operable time. This composition is, however, not necessarily excellent in penetrability into a collagen layer of dentin and may cause a reduction in bond strength, and therefore improvement in this respect has been desired.

When such a dental adhesive is allowed to act on dentin, it is important for the dental adhesive to have a decalcifying effect that allows a dentin surface to be dissolved with an acidic component, a penetration effect that allows a monomer component to penetrate into a collagen layer of dentin, and a curing effect that allows the monomer component thus penetrated to solidify to form a hybrid layer (hereinafter also referred to as a "resin-impregnated layer") with collagen.

It has been studied so far to simplify the form of application of the dental adhesive from a three-component three-step type in which the aforementioned decalcifying effect, penetration effect, and curing effect are applied sequentially, to a two-component two-step type in which the decalcifying effect and the penetration effect are integrated, and further to a one-component one-step type in which the decalcifying effect, penetration effect, and curing effect are all combined together. All the forms of application require compositions that can be used for dental adhesives that are excellent in adhesive properties. Therefore, there is a demand for a polymerizable monomer that is used as a component of the composition and that imparts the excellent adhesive properties.

DISCLOSURE OF INVENTION

The present invention is intended to provide a polymerizable composition that imparts excellent adhesive properties to a tooth structure (particularly dentin) when it is applied as a dental material, and a polymerizable monomer that is used as a component of the polymerizable composition. The present invention also is intended to provide a dental material that is excellent in adhesive properties to a tooth structure (particularly dentin).

The present invention that has achieved the above-mentioned objects is a compound (A) represented by formula (1):

[Chemical Formula 1]

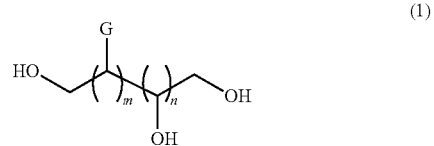

where G indicates a polymerizable group, m indicates an integer of 2 or more, n indicates an integer of 1 or more, and the sequence order of m units having a polymerizable group and n units having a hydroxyl group is arbitrary.

Preferably, the polymerizable groups in the compound (A) each are a group represented by formula (2), (3), or (4):

[Chemical Formula 2]

[Chemical Formula 3]

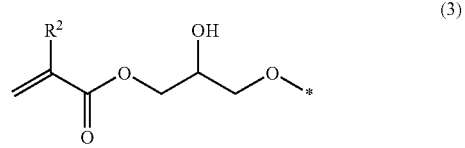

[Chemical Formula 4]

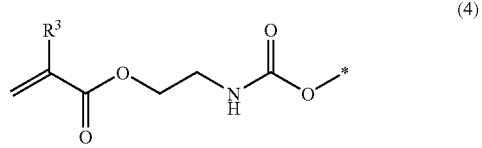

where $R^1$, $R^2$ and $R^3$ each indicate a hydrogen atom or an aliphatic hydrocarbon group having 1 to 10 carbon atoms and "*" indicates a bond.

Preferably, the compound (A) is a compound represented by formula (5):

[Chemical Formula 5]

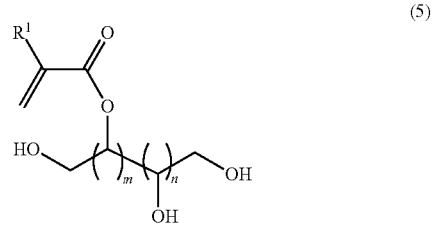

{hereinafter, also referred to as compound (5)}, where $R^1$ denotes a hydrogen atom or an aliphatic hydrocarbon group having 1 to 10 carbon atoms, m denotes an integer of 2 or more, n denotes an integer of 1 or more, and the sequence order of m units having an ester group and n units having a hydroxyl group is arbitrary. In this case, it is more preferable that $R^1$ be a hydrogen atom or methyl group, and m be 2 and n be 2.

Most preferably, the compound (A) is a compound represented by formula (6):

[Chemical Formula 6]

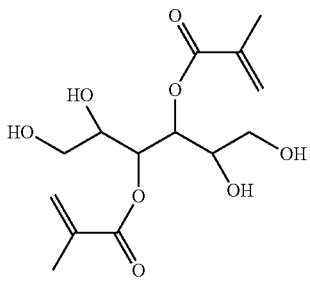

(6)

{hereinafter, also referred to as compound (6)}; or a compound represented by formula (7):

[Chemical Formula 7]

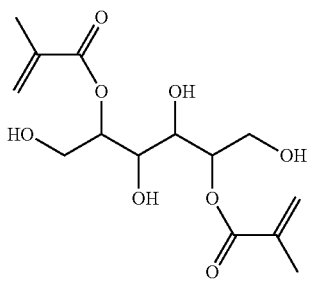

(7)

{hereinafter, also referred to as compound (7)}.

The present invention is also a polymerizable composition containing the compound (A) as a polymerizable monomer component. It is preferable that the polymerizable composition further contain, as a polymerizable monomer component, at least one selected from a polymerizable monomer (B) having one polymerizable group and at least one hydroxyl group, a polymerizable monomer (C) having an acidic group, and a crosslinkable polymerizable monomer (D). Moreover, the polymerizable composition preferably contains a polymerization initiator (E), a polymerization accelerator (F), a filler (G) or a solvent (H).

Furthermore, the present invention includes a dental primer, dental bonding material, dental cement, and dental composite resin, each of which contains the polymerizable composition.

Since the compound (A) of the present invention has a plurality of polymerizable groups and hydrophilic groups, it is useful for the applications that require the compound (A) to be curable and applications that require a polymer of the compound (A) to be hydrophilic. A polymerizable composition that contains the compound (A) of the present invention is useful for various applications including dental applications. Particularly, a dental primer, bonding material, cement, and composite resin using the polymerizable compositions are exceptionally excellent in adhesive properties to tooth structures.

BEST MODE FOR CARRYING OUT THE INVENTION

Compound (A)

The compound (A) has a main skeleton like sugar alcohols as shown in the formula (1). Such a main skeleton can contain polymerizable groups and hydroxyl groups in a high density, so that it is advantageous in polymerizability and hydrophilicity. In addition, since sugar alcohols (particularly, sugar alcohols having 5 to 20 carbon atoms: such as xylitol, ribitol, and arabinitol, each of which is a sugar alcohol having 5 carbon atoms; mannitol, sorbitol, and iditol, each of which is a sugar alcohol having 6 carbon atoms; and maltitol, a sugar alcohol having 12 carbon atoms) can be used as a raw material, the raw material is easily available, so that it is advantageous in production.

The compound (A) has a structure where a part of the secondary hydroxyl groups of the main skeleton like sugar alcohols is substituted by polymerizable groups, and the compound (A) contains two primary hydroxyl groups and at least one secondary hydroxyl group. Accordingly, the compound (A) contains at least three hydroxyl groups, thereby having a high hydrophilicity, so that it is highly advantageous in hydrophilic interaction, for example, interaction with a collagen layer of dentin. Thus, when a composition containing the compound (A) is applied as a dental application, it is possible for the composition to impart high adhesive properties to tooth structures. Further, two of the at least three hydroxyl groups are primary hydroxyl groups, so that it is highly advantageous in hydrophilicity.

The compound (A) has at least two polymerizable groups, and can function as a polymerizable monomer. When a composition containing the compound (A) is used for a dental application, these polymerizable groups are polymerized and thereby the composition is cured to be able to function as, for example, bonding material, or composite resin. Furthermore, since the number of the polymerizable groups is two or more, the compound (A) has crosslinkability. Accordingly, the composition has high curability and the cured product has high mechanical strength.

With respect to the compound (A), the polymerizable group denotes a group including a radical polymerizable functional group and examples thereof include a group including a vinyl group. Particularly, from the viewpoint of polymerization reactivity, the group represented by the following formula (2), (3), or (4) is preferable as the polymerizable group. Among these, from the viewpoint of ease of introduction into the compound (A), a group represented by formula (2) is most preferable.

[Chemical Formula 8]

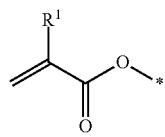

(2)

[Chemical Formula 9]

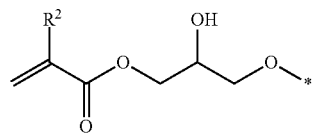

(3)

[Chemical Formula 10]

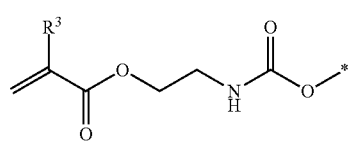

(4)

In the above formulae, $R^1$, $R^2$, and $R^3$ each indicate a hydrogen atom or an aliphatic hydrocarbon group having 1 to 10 carbon atoms and "*" indicates a bond. Examples of the aliphatic hydrocarbon group having 1 to 10 carbon atoms include an alkyl group having 1 to 10 carbon atoms, an alkenyl group having 2 to 10 carbon atoms, and an alkynyl group having 2 to 10 carbon atoms.

The alkyl group having 1 to 10 carbon atoms may be any one of linear, branched, and cyclic, and examples thereof include a methyl group, ethyl group, n-propyl group, isopropyl group, cyclopropyl group, n-butyl group, isobutyl group, sec-butyl group, tert-butyl group, cyclobutyl group, n-pentyl group, isopentyl group, neopentyl group, tert-pentyl group, cyclopentyl group, n-hexyl group, isohexyl group, cyclohexyl group, n-heptyl group, cycloheptanyl group, n-octyl group, 2-ethylhexyl group, cyclooctanyl group, n-nonyl group, cyclononanyl group, and n-decyl group.

The alkenyl group having 2 to 10 carbon atoms may be any one of linear, branched, and cyclic, and examples thereof include a vinyl group, allyl group, methylvinyl group, propenyl group, butenyl group, pentenyl group, hexenyl group, cyclopropenyl group, cyclobutenyl group, cyclopentenyl group, and cyclohexenyl group.

The alkynyl group having 2 to 10 carbon atoms may be any one of linear, branched, and cyclic, and examples thereof include ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, and 1-ethyl-3-butynyl.

When the compound (A) is used in, for example, dental applications, radical polymerization is performed. Accordingly, it is preferable from the viewpoint of radical polymerization reactivity that $R^1$, $R^2$, and $R^3$ each be a hydrogen atom or a methyl group. Furthermore, when the compound (A) is used in a dental composition, the polymerizable group may be detached from the compound (A) by, for example, hydrolysis. When the stimulativeness of the detached polymerizable group to a biological body is taken into account, it is preferable that the polymerizable group include a methacryloyloxy group. Therefore, it is more preferable that $R^1$, $R^2$, and $R^3$ each be a methyl group.

The compound (A) includes at least two polymerizable groups, and the at least two polymerizable groups may be identical to or different from each other.

In formula (1), m denotes an integer of 2 or more, preferably 2 to 5, more preferably 2 to 4, and most preferably 2. n denotes an integer of 1 or more, preferably 1 to 5, more preferably 2 to 4, and most preferably 2. The total of m and n is 3 to 18, preferably 3 to 9, more preferably 4 to 8, and most preferably 4. The sequence order of m units having an ester group and n units having a hydroxyl group is arbitrary.

Preferably, the compound (A) has a structure represented by the following formula (5):

[Chemical Formula 11]

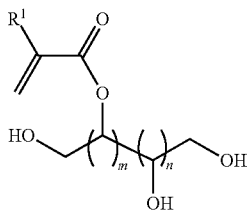

(5)

The compound represented by formula (5) (namely, compound (5)) is excellent in any of hydrophilicity, curability, and safety to biological bodies, and it is a particularly useful polymerizable monomer for dental applications.

More preferably, the compound (A) has a structure represented by formula (6) or formula (7). In other words, the compound (A) is preferably compound (6) or compound (7).

[Chemical Formula 12]

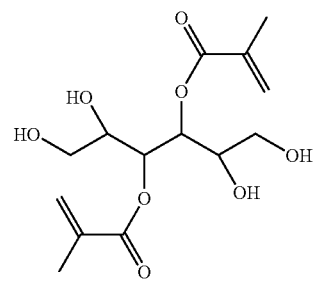

(6)

[Chemical Formula 13]

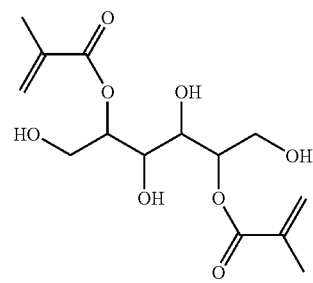

(7)

Subsequently, a production process of the compound (A) is described hereinafter. As described above, the compound (A) has a structure where a part of the secondary hydroxyl groups of the main skeleton like sugar alcohols is substituted by polymerizable groups. In this case, a general method where sugar alcohol, and a carboxylic acid or an acid halide having the polymerizable groups are simply reacted to be esterified causes introduction of the polymerizable groups into the primary hydroxyl groups, because the primary hydroxyl groups have a higher reactivity than the secondary hydroxyl groups. Thus, the compound (A) cannot be obtained by a general method. Therefore, in order to produce the compound (A), it is preferable that the compound (A) be produced by performing a step (a) where, using a compound in which the primary hydroxyl groups of the sugar alcohol are protected beforehand as a raw material, the compound and a compound containing polymerizable groups are esterified, and a step (b) where the protecting groups of the primary hydroxyl groups of the resultant ester compound are deprotected.

Examples of the compound containing polymerizable groups to be preferably used include, when the polymerizable groups are represented by formula (2), a compound containing polymerizable groups represented by the following formula (8) {hereinafter, also referred to as a compound (8)} or the derivatives thereof, when the polymerizable groups are represented by formula (3), a compound containing polymerizable groups represented by the following formula (9), and when the polymerizable groups are represented by formula (4), a compound containing polymerizable groups represented by the following formula (10).

[Chemical Formula 14]

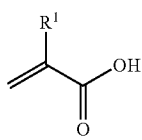

(8)

[Chemical Formula 15]

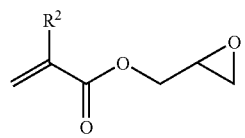

(9)

[Chemical Formula 16]

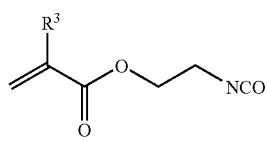

(10)

When the compound (A) is particularly the compound (5), especially the compound (6) or the compound (7), the compound (8) and the derivative of the compound (8) are used preferably as the compound containing polymerizable groups. The derivative of the compound (8) is not particularly limited but an acid halide or acid anhydride is used preferably. When the reactivity with sugar alcohol is taken into account, an acid halide is used more preferably. Furthermore, among the acid halides, acid chloride is used particularly preferably when availability and storage stability of the compound are taken into account. The production process including these steps allows a polymerizable monomer to be obtained with high yield and therefore is suitable for industrial production.

The compound in which primary hydroxyl groups of sugar alcohol are protected beforehand can be obtained as a commercially available product, for example, 1,2:5,6-di-O-isopropylidene-D-mannitol and 1,3:4,6-di-O-benzylidene-D-mannitol. Furthermore, it also can be produced by carrying out a step of protecting the primary hydroxyl groups of sugar alcohol. In a compound in which primary hydroxyl groups of sugar alcohol are protected beforehand, it is preferable that a part of hydroxyl groups other than the primary hydroxyl groups be protected while a plurality of hydroxyl groups are allowed to remain. In this manner, a structure having at least three hydroxyl groups is obtained easily.

The step of protecting the primary hydroxyl groups of sugar alcohol can be carried out by performing a known reaction for introducing protecting groups.

It is advantageous to select a group that is introduced preferentially into a primary hydroxyl group, as a protecting group for the primary hydroxyl groups of sugar alcohol. Furthermore, for the protecting group, it is advantageous to select one that tends not to undergo a deprotection reaction during the esterification reaction and tends not to allow the ester bond to be cleaved during the deprotection reaction. From these viewpoints, protecting groups that are used preferably are ether protecting groups, silyl ether protecting groups, and acetal protecting groups. Ether protecting groups that are used more preferably are a 1-ethoxyethyl ether group and triphenylmethyl ether group. Silyl ether protecting groups that are used more preferably are a triisopropylsilyl ether group, t-butyldimethylsilyl ether group, and t-butyldiphenylsilyl ether group. Each of these protecting groups can be introduced preferentially into a primary hydroxyl group and can be deprotected under a mild acidic condition, and therefore it has an advantage that deprotection can be achieved without cleaving the ester bond. On the other hand, acetal protecting groups that are used more preferably are an isopropylidene group, cycloheptylidene group, benzylidene group, and p-methoxybenzylidene group. When using an acetal protecting group, it not only can be introduced preferentially into a primary hydroxyl group but also can protect two or more hydroxyl groups including the primary hydroxyl group at the same time. Accordingly, the acetal protecting group is especially suitable for synthesis of the compound (A) of the present invention. Therefore, among the ether protecting groups, silyl ether protecting groups, and acetal protecting groups, the acetal protecting groups are used further preferably. Moreover, from the viewpoints that deprotection is possible under a particularly mild acidic condition and a byproduct produced at the time of deprotection can be removed easily, an isopropylidene group is used particularly preferably.

The step of esterifying a compound in which primary hydroxyl groups of sugar alcohol are protected beforehand and a compound having a polymerizable group (e.g. the compound (8) or a derivative thereof) can be carried out according to a known method. For the esterification reaction, it is important to select suitable reaction conditions (particularly, the temperature condition and the type of catalyst) under which a deprotection reaction tends not to occur, with consideration given to the type of the protecting group. Furthermore, it is important to select the reaction conditions (particularly, the amounts of the compound in which primary hydroxyl groups of sugar alcohol are protected beforehand and the compound having a polymerizable group to be used) so that after the esterification reaction, a plurality of ester bonds are formed and the total number of the protected hydroxyl groups and unreacted hydroxyl groups is at least three, in one molecule.

The step of deprotecting the protecting groups of the primary hydroxyl groups of the resultant ester compound may be carried out according to a known method depending on the type of the protecting group. In this case, it is important to select reaction conditions (particularly, the temperature condition and the type of catalyst) under which the ester bond tends not to be cleaved. As described above, when the ether protecting groups, silyl ether protecting groups, and acetal protecting groups that are preferable as the protecting group of the primary hydroxyl group are used, all of them can be deprotected under mild acidic conditions and therefore deprotection can be performed without allowing the ester bond to be cleaved. Furthermore, the silyl ether protecting groups can be deprotected with extremely high selectivity by the use of a fluorine-containing compound such as TBAF (tetrabutylammonium fluoride) and thus are highly useful. In the case of deprotection under an acidic condition, for example, mineral acids such as hydrochloric acid and sulfuric acid and aqueous solutions thereof organic acids such as formic acid, acetic acid, and trifluoroacetic acid and aqueous solutions thereof, and cation exchange resin are used preferably. Among these, since the acidity is suitable and deprotection can be performed with cleavage of the ester bond being prevented efficiently, organic acids such as formic acid, acetic acid, and trifluoroacetic acid and aqueous solutions thereof are more preferable, and formic acid, acetic acid, and aqueous solutions thereof are further preferable.

Since the compound (A) has a plurality of polymerizable groups and three or more hydroxyl groups, it is excellent in crosslinking reactivity and can interact strongly with a compound having a hydrophilic group. Accordingly, when the polymerizable monomer is mixed with a suitable component into a polymerizable composition, the composition thus obtained exhibits excellent curability and adhesive properties in various applications including dental applications. Hereinafter, embodiments of the polymerizable composition will be described in detail.

Polymerizable Composition

The polymerizable composition according to the present invention is a composition containing the compound (A) as a polymerizable monomer component. The components other than the compound (A) may be selected appropriately depending on the application of the polymerizable composition. For example, the polymerizable composition may be composed from a composition containing a known polymerizable monomer that is crosslinkable by replacing the known polymerizable monomer with the compound (A).

Examples of the components contained in the polymerizable composition of the present invention other than the compound (A) include polymerizable monomer components, such as a polymerizable monomer (B) containing one polymerizable group and at least one hydroxyl group, a polymerizable monomer (C) having an acidic group, and a crosslinkable polymerizable monomer (D), a polymerization initiator (E), a polymerization accelerator (F), a filler (G), and a solvent (H).

The amount of compound (A) to be added may be determined appropriately according to the application of the polymerizable composition. Preferably, 1 to 99 parts by mass of compound (A) is contained in 100 parts by mass of the whole amount of polymerizable monomer components. When a composition in which the amount of the compound (A) to be added is in such a range is used as a dental composition, there are advantages that penetrability into a collagen layer of dentin is excellent and bond strength is high. When the amount of compound (A) to be added is less than 1 part by mass, bond strength may be reduced and bond durability also may be reduced. Therefore, the amount is more preferably at least 2 parts by mass and further preferably at least 5 parts by mass. On the other hand, the amount of compound (A) to be added exceeding 99 parts by mass results in insufficient decalcification and sufficiently high bond strength may not be obtained. Therefore the amount is more preferably 98 parts by mass or less and further preferably 95 parts by mass or less.

In the following description, terms "monofunctional", "bifunctional", and "trifunctional" are used and the terms "monofunctional", "bifunctional", and "trifunctional" indicate that one, two, and three polymerizable groups each are contained in one molecule. Preferably, these polymerizable groups are groups that are radical-copolymerizable with a vinyl group of a compound (1), that has been substituted by $R^1$.

Polymerizable monomer (B) having one polymerizable group and at least one hydroxyl group Preferably, the polymerizable composition containing the compound (A) of the present invention contains a polymerizable monomer (B) having one polymerizable group and at least one hydroxyl group. When the polymerizable composition contains the polymerizable monomer (B), particularly when it is used as a dental composition, excellent bond strength is obtained. Since the polymerizable monomer (B) has a polymerizable group, not only radical polymerization can occur but also copolymerization with another monomer can occur. The polymerizable monomer (B) having one polymerizable group and at least one hydroxyl group is not particularly limited. The polymerizable group is preferably a group that is radical-copolymerizable with a vinyl group of the compound (1), that has been substituted by $R^1$. From the viewpoint of ease of radical polymerization, the polymerizable group is preferably a (meth)acrylic group or (meth)acrylamide group. The polymerizable monomer (B) is used preferably as a component of a dental composition. However, since the inside of an oral cavity has a humid environment, the polymerizable group may be detached by, for example, hydrolysis. When consideration is given to stimulativeness of a detached polymerizable group to a biological body, the polymerizable group is preferably a methacrylic group or methacrylamide group.

The polymerizable monomer (B) has at least one hydroxyl group and therefore has excellent hydrophilicity, and it is a monofunctional polymer monomer having one polymerizable group. Accordingly, when a composition of the present invention containing a compound (A) and a polymerizable monomer (B) is used as a dental composition, an effect that the penetrability into a collagen layer of dentin is further excellent also is obtained.

Examples of the polymerizable monomer (B) include 2-hydroxyethyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, and N,N-(dihydroxyethyl) (meth)acrylamide. Among these, from the viewpoint of improving the penetrability into a collagen layer of dentin, 2-hydroxyethyl(meth)acrylate, 3-hydroxypropyl(meth)acrylate, glycerol mono(meth)acrylate, and erythritol mono (meth)acrylate are preferable and 2-hydroxyethylmethacrylate is particularly preferable.

The amount of polymerizable monomer (B) to be added is not particularly limited, but it is preferable that 1 to 90 parts by mass of polymerizable monomer (B) be contained with respect to 100 parts by mass of the whole amount of polymerizable monomer components. When a composition in which the amount of polymerizable monomer (B) to be added is in such a range is used as a dental composition, both excellent penetrability into a collagen layer of dentin and excellent bond strength are obtained and it thus is preferable. When the amount of polymerizable monomer (B) to be added is less than 1 part by mass, contribution of the polymerizable monomer (B) to penetration into a collagen layer of dentin may not be obtained and the bond strength may be reduced. The amount of polymerizable monomer (B) to be added is more preferably at least 3 parts by mass, further preferably at least 5 parts by mass, and particularly preferably at least 7 parts by mass. On the other hand, when the amount of polymerizable monomer (B) to be added exceeds 90 parts by mass, sufficiently high curability cannot be obtained and therefore the mechanical strength of the cured product may be reduced. Accordingly, the bond strength may be reduced. The amount of polymerizable monomer (B) to be added is more preferably 80 parts by mass or less, further preferably 75 parts by mass or less, and particularly preferably 70 parts by mass or less.

Polymerizable Monomer (C) Having Acidic Group

Preferably, the polymerizable composition of the present invention contains 1 to 90 parts by mass of polymerizable monomer (C) having an acidic group in 100 parts by mass of the whole amount of polymerizable monomer components. When a composition in which the amount of polymerizable monomer (C) having an acidic group to be added is in such a range is used as a dental composition, it has advantages that, for example, pretreatments such as an acid etching treatment and a primer treatment are not necessary, since the polymerizable monomer (C) itself that has an acidic group has an acid-etching effect and a primer treatment effect. Accordingly, a combination with a polymerizable monomer (C) having an acidic group makes it possible to provide a bonding material that is simple to use and has high bond strength and excellent bond durability, particularly preferably a one-component bonding material. When the amount of polymerizable monomer (C) having an acidic group to be added is less than 1 part by weight, the acid-etching effect or primer treatment effect may not be obtained. Therefore, the amount is more preferably at least 2 parts by mass and further preferably at least 5 parts by mass. On the other hand, when the amount of polymerizable monomer (C) having an acidic group to be added exceeds 90 parts by mass, sufficiently high curability may not be obtained and therefore the adhesive properties may be deteriorated. Accordingly, the amount is more preferably 80 parts by mass or less and further preferably 70 parts by mass or less.

The polymerizable monomers (C) having acidic groups are not particularly limited. Examples thereof include a monofunctional polymerizable monomer having one carboxyl group or an acid anhydride group thereof in the molecule, a monofunctional polymerizable monomer having a plurality of carboxyl groups or an acid anhydride group thereof in the molecule, and a monofunctional polymerizable monomer having a phosphinyloxy group or phosphonooxy group in the molecule (also referred to as a monofunctional radical polymerizable phosphoric acid ester).

Examples of the monofunctional polymerizable monomer having one carboxyl group or an acid anhydride group thereof in the molecule include (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyethyl naphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-4-aminosalicylic acid, and compounds obtained by converting the carboxyl group of these compounds into an acid anhydride group.

Examples of the monofunctional polymerizable monomer having a plurality of carboxyl groups or an acid anhydride group thereof in the molecule include 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)-propyl succinate, 4-(2-(meth)acryloyloxyethyl)trimeritate anhydride, 4-(2-(meth)acryloyloxyethyl)trimeritate, 4-(meth)acryloyloxyethyl trimeritate, 4-(meth)acryloyloxybutyl trimeritate, 4-(meth)acryloyloxyhexyl trimeritate, 4-(meth)acryloyloxydecyl trimeritate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, 4-(meth)acryloyloxyethylnaphthalene-1,8-tricarboxylic acid anhydride, 9-(meth)acryloyloxynonane-1,1-dicarboxylic acid, 13-(meth)acryloyloxytridecane-1,1-dicarboxylic acid, and 11-(meth)acrylamideundecane-1,1-dicarboxylic acid.

Examples of the monofunctional polymerizable monomer having a phosphinyloxy group or phosphonooxy group in the molecule (also referred to as a monofunctional radical polymerizable phosphoric acid ester) include 2-(meth)acryloyloxyethyl dihydrogenphosphate, 2-(meth)acryloyloxyethylphenyl hydrogenphosphate, 10-(meth)acryloyloxydecyl dihydrogenphosphate, 6-(meth)acryloyloxyhexyl dihydrogenphosphate, 2-(meth)acryloyloxyethyl-2-bromoethyl hydrogenphosphate, and 2-(meth)acrylamideethyl dihydrogenphosphate.

Examples of other monofunctional polymerizable monomer having an acidic group include a monofunctional polymerizable monomer having a sulfo group in the molecule such as 2-(meth)acrylamide-2-methylpropanesulfonic acid and 10-sulfodecyl(meth)acrylate.

Crosslinkable Polymerizable Monomer (D)

Preferably, the polymerizable composition of the present invention contains 1 to 90 parts by mass of crosslinkable polymerizable monomer (D) in 100 parts by mass of the whole amount of polymerizable monomer components. When a composition in which the amount of a crosslinkable polymerizable monomer (D) to be added is in such a range is used as a dental composition, it has advantages such as a further improvement in bond strength. When the amount of crosslinkable polymerizable monomer (D) to be added is less than 1 part by mass, sufficiently high bond strength may not be obtained. Therefore, the amount is more preferably at least 2 parts by mass and further preferably at least 5 parts by mass. On the other hand, when the amount of crosslinkable polymerizable monomer (D) to be added exceeds 90 parts by mass, the composition may not penetrate sufficiently into a collagen layer of dentin and thereby high bond strength may not be obtained. Therefore, the amount is more preferably 80 parts by mass or less and further preferably 70 parts by mass or less.

Crosslinkable polymerizable monomers (D) are not particularly limited. Examples thereof include an aromatic compound-based bifunctional polymerizable monomer, an aliphatic compound-based bifunctional polymerizable monomer, and trifunctional or higher polymerizable monomers.

Examples of the aromatic compound-based bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)

propane, 2,2-bis(4-(meth)acryloyloxypentaethoxyphenyl) propane, 2,2-bis(4-(meth)acryloyloxydipropoxyphenyl)propane, 2-(4-(meth)acryloyloxydiethoxyphenyl) -2-(4-(meth) acryloyloxyethoxyphenyl)-propane, 2-(4-(meth) acryloyloxydiethoxyphenyl) -2-(4-(meth) acryloyloxytriethoxy-phenyl)propane, 2-(4-(meth) acryloyloxydipropoxyphenyl)-2 -(4-(meth) acryloyloxytriethoxy-phenyl)propane, 2,2-bis(4-(meth) acryloyloxypropoxyphenyl)propane, 2,2-bis(4-(meth) acryloyloxyisopropoxyphenyl)propane, and 1,4-bis(2-(meth)acryloyloxyethyl)pyromeritate.

Examples of the aliphatic compound-based bifunctional polymerizable monomer include ethylene glycol di(meth) acrylate, diethylene glycol di(meth)acrylate, triethylene glycol di(meth)acrylate, propylene glycol di(meth)acrylate, butylene glycol di(meth)acrylate, neopentyl glycol di(meth) acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth) acrylate, 1,2-bis(3-methacryloyloxy-2-hydroxypropoxy) ethane, and 2,2,4-trimethylhexamethylenebis(2-carbamoyloxyethyl)dimethacrylate (commonly known as "UDMA").

Examples of the trifunctional or higher polymerizable monomers include trimethylolpropane tri(meth)acrylate, trimethylolethane tri(meth)acrylate, trimethylolmethane tri (meth)acrylate, pentaerythritol tri(meth)acrylate, pentaerythritol tetra(meth)acrylate, dipentaerythritol tetra(meth) acrylate, dipentaerythritol penta(meth)acrylate, dipentaerythritol hexa(meth)acrylate, N,N-(2,2,4-trimethylhexamethylene)bis[2-(aminocarboxy)propane-1,3-diol] tetramethacrylate, and 1,7-diacryloyloxy-2,2,6,6-tetraacryloyloxymethyl-4-oxyheptane.

The polymerizable composition of the present invention may contain a polymerizable monomer other than the aforementioned (A), (B), (C), and (D) as required.

Polymerization Initiator (E)

A polymerization initiator (E) used in the present invention can be selected from polymerization initiators commonly used in the industrial field. Among them, polymerization initiators used for dental applications are used preferably. Particularly, photopolymerization initiators and chemical polymerization initiators are used independently or two or more of them are used in suitable combination.

Examples of the photopolymerization initiator include (bis)acylphosphine oxides, water-soluble acylphosphine oxides, thioxanthones or the quaternary ammonium salts of thioxanthones, ketals, alpha-diketones, coumarins, anthraquinones, benzoin alkyl ether compounds, and alpha-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoyl-methoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl) phosphonate. Examples of the bisacylphosphine oxides include bis-(2,6-dichlorobenzoyl)phenylphosphine oxide, bis-(2,6-dichlorobenzoyl) -2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl) -2,5-dimethylphenylphosphine oxide, bis-(2,4,6-trimethylbenzoyl)phenylphosphine oxide, and (2,5,6-trimethylbenzoyl) -2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 or JP 57(1982)-197289 A.

Specific examples of the aforementioned water-soluble acylphosphine oxides include sodium monomethylacetylphosphonate, sodium monomethyl(1-oxopropyl) phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl) pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl) phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl(1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the above-mentioned photopolymerization initiators include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of ketals used as the photopolymerization initiator include benzyl dimethyl ketal and benzyl diethyl ketal.

Examples of the alpha-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the coumarin compound used as the aforementioned photopolymerization initiator include compounds described in JP 9(1997)-3109 A and JP 10(1998)-245525 A such as 3,3'-carbonylbis(7-diethylamino)coumarin, 3-(4-methoxybenzoyl)coumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p -nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo [f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazole-2-ilidene)acetyl]coumarin, 3-[(1-methylnaphtho[1,2-d]thiazole-2-ilidene)acetyl]coumarin, 3,3'-carbonylbis(6-methoxycoumarin), 3,3'-carbonylbis(7-acetoxycoumarin), 3,3' -carbonylbis(7-dimethylaminocoumarin), 3-(2-benzothiazoyl)-7-(die thylamino) coumarin, 3-(2-benzothiazoyl)-7-(dibutylamino)coumarin, 3-(2-benzimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl) aminocoumarin, 10-[3-[4-(dimethylamino)phenyl]-1-oxo-2-propenyl]-2,3,6,7-1,1,7,7-tetramethyl1H, 5H, 11H-[1] benzopyrano[6,7,8-ij] quinolizine-11-one, and 10-(2-benzothiazoyl)-2,3,6,7-tetrahydro-1,1,7,7-tetramethyl1H, 5H, 11H-[1]-benzopyrano[6,7,8-ij]quinolizin-11-one.

Among the above-mentioned coumarin compounds, particularly 3,3'-carbonylbis(7-diethylaminocoumarin) and 3,3'-carbonylbis(7-dibutylaminocoumarin) are suitable.

Examples of the anthraquinones used as the aforementioned photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers used as the aforementioned photopolymerization initiator include benzoin methyl ether, benzoin ethyl ether, benzoin isopropyl ether, and benzoin isobutyl ether.

Examples of the alpha-aminoketones used as the aforementioned photopolymerization initiator include 2-methyl-1-[4-(methylthio)phenyl]-2-morpholinopropane-1-one.

Preferably, among these photopolymerization initiators, at least one selected from the group consisting of (bis)acylphosphine oxides, salts thereof, alpha-diketones, and coumarin compounds is used. This makes it possible to obtain a polymerizable composition that has excellent photocurability in visible and near-ultraviolet ranges and sufficiently high photocurability regardless of which light source among a halogen lamp, light-emitting diode (LED), and xenon lamp is used.

Among the polymerization initiators (E) used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of ketone peroxide used as the chemical polymerization initiator include methyl ethyl ketone peroxide, methyl isobutyl ketone peroxide, methylcyclohexanone peroxide, and cyclohexanone peroxide.

Examples of hydroperoxide used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of peroxyester used as the chemical polymerization initiator include alpha-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of peroxydicarbonate used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxide is used preferably from the viewpoint of a comprehensive balance of safety, storage stability, and radical production ability, and among these, benzoyl peroxide is used particularly preferably.

The amount of polymerization initiator (E) to be added in the present invention is not particularly limited. However, from the viewpoint of, for example, curability of the resultant composition, it is preferable that 0.001 to 30 parts by mass of polymerization initiator (E) be contained with respect to 100 parts by mass of the whole amount of polymerizable monomer components. When the amount of polymerization initiator (E) to be added is less than 0.001 part by mass, polymerization may not proceed sufficiently and thereby bond strength may be reduced. Therefore, the amount is more preferably at least 0.05 part by mass. On the other hand, when the amount of polymerization initiator (E) to be added exceeds 30 parts by mass, in the case where the polymerization initiator itself has low polymerization performance, sufficiently high bond strength may not be obtained and further precipitation from the composition may occur. Therefore, the amount is more preferably 20 parts by mass or less.

In a preferred embodiment, the above polymerization initiator (E) is used together with a polymerization accelerator (F). Examples of the polymerization accelerator (F) used in the present invention include amines, sulfinic acids and salts thereof, borate compounds, barbituric acid derivatives, triazine compounds, copper compounds, tin compounds, vanadium compounds, halogen compounds, aldehydes, thiol compounds, sulfite, bisulfite, and thiourea compounds.

Amines used as the polymerization accelerator (F) can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of sulfinic acid and salt thereof used as the polymerization accelerator (F) include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

The borate compound used as the polymerization accelerator (F) is preferably an arylborate compound. Specific examples of arylborate compounds that are used preferably include, as a borate compound having one aryl group in one molecule, sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (each alkyl group is at least one selected from the group consisting of, for example, an n-butyl group, an n-octyl group, and an n-dodecyl group).

Examples of the borate compound having two aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of dialkyldiphenylboron, dialkyldi(p- chlorophenyl)boron, dialkyldi(p-fluorophenyl)boron, dialkyldi(3,5-bistrifluoromethyl)phenylboron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (each alkyl group is at least one selected from the group consisting of, for example, an n-butyl group, an n-octyl group, and an n-dodecyl group).

Examples of the borate compound having three aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of monoalkyltriphenylboron, monoalkyltri(p-chlorophenyl)boron, monoalkyltri(p-fluorophenyl)boron, monoalkyltri(3,5-bistrifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl)boron (each alkyl group is one selected from, for example, an n-butyl group, an n-octyl group, and an n-dodecyl group).

Furthermore, examples of the borate compound having four aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, (3,5-bistrifluoromethyl)phenyltriphenylboron, (p-nitrophenyl)triphenylboron, (m-butyloxyphenyl)triphenylboron, (p-butyloxyphenyl)triphenylboron, (m-octyloxyphenyl)triphenylboron, and (p-octyloxyphenyl)triphenylboron.

More preferably, from the viewpoint of storage stability, among these arylborate compounds, a borate compound having three or four aryl groups in one molecule is used. Furthermore, one of these arylborate compounds can be used or two or more of them can be used in mixture.

Examples of a barbituric acid derivative used as the polymerization accelerator (F) include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids, as well as salts thereof (particularly, alkali metals or alkaline earth metals are preferable). Examples of salts of these barbituric acids include sodium 5-butylbarbiturate, sodium 1,3,5-trimethylbarbiturate, and sodium 1-cyclohexyl-5-ethylbarbiturate.

Examples of particularly preferable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compound used as the polymerization accelerator (F) include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Particularly preferable ones among the triazine compounds described above as examples are 2,4,6-tris(trichloromethyl)-s-triazine in terms of polymerization activity and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine in terms of storage stability. One of the above-mentioned triazine compounds may be used or two or more of them may be used in mixture.

Examples of the copper compound used preferably as the polymerization accelerator (F) include copper acetylacetonate, copper (II) acetate, copper oleate, copper (II) chloride, and copper (II) bromide.

Examples of the tin compound used as the polymerization accelerator (F) include di-n-butyltin dimalate, di-n-octyltin dimalate, di-n-octyltin dilaurate, and di-n-butyltin dilaurate. Particularly preferable tin compounds are di-n-octyltin dilaurate and di-n-butyltin dilaurate.

The vanadium compound used as the polymerization accelerator (F) is preferably one of tetravalent and/or pentavalent vanadium compounds. Examples of the tetravalent and/or pentavalent vanadium compounds include compounds described in JP 2003-96122 A such as divanadium (IV) tetroxide, vanadyl (IV) acetylacetonate, vanadyl (IV) oxalate, vanadyl (IV) sulfate, oxobis(1-phenyl-1,3-butanedionate)vanadium (IV), bis(maltolato)oxovanadium (IV), vanadium (V) pentoxide, sodium metavanadate (V), and ammonium metavanadate (V).

Examples of the halogen compound used preferably as the polymerization accelerator (F) include dilauryldimethylammoniumchloride, lauryldimethylbenzylammoniumchloride, benzyltrimethylammoniumchloride, tetramethylammoniumchloride, benzyldimethylcetylammoniumchloride, and dilauryldimethylammoniumbromide.

Examples of aldehydes used as the polymerization accelerator (F) include terephthalaldehyde and a benzaldehyde derivative. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator (F) include 3-mercaptopropyltrimethoxysilane, 2-mercaptobenzooxazol, decanethiol, and thiobenzoic acid.

Examples of sulfite used as the polymerization accelerator (F) include sodium sulfite, potassium sulfite, calcium sulfite, and ammonium sulfite.

Examples of bisulfate used as the polymerization accelerator (F) include sodium bisulfate and potassium bisulfate.

Examples of the thiourea compound used as the polymerization accelerator (F) include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

The amount of polymerization accelerator (F) to be added in the present invention is not particularly limited. However, from the viewpoints of, for example, curability of the resultant composition, it is preferable that 0.001 to 30 parts by mass of polymerization accelerator (F) be contained with respect to 100 parts by mass of the whole amount of polymerizable monomer components. When the amount of polymerization accelerator (F) to be added is less than 0.001 part by mass, polymerization may not proceed sufficiently and bond strength may be reduced. Therefore, the amount is more preferably at least 0.05 part by mass. On the other hand, when the amount of polymerization accelerator (F) to be added exceeds 30 parts by mass, in the case where the polymerization initiator itself has low polymerization performance, sufficiently high bond strength may not be obtained and further precipitation from the composition may occur. Therefore, the amount is more preferably 20 parts by mass or less.

Filler (G)

Preferably, a filler (G) further is mixed into a polymerizable composition of the present invention depending on the embodiment. Generally, such fillers are divided roughly into organic fillers, inorganic fillers, and organic-inorganic composite fillers. Examples of materials for the organic fillers include polymethylmethacrylate, polyethylmethacrylate, a methylmethacrylate-ethylmethacrylate copolymer, cross-linked polymethylmethacrylate, cross-linked polyethylmethacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used independently or a mixture of two or more of them may be used. The shapes of the organic fillers are not particularly limited, and particle sizes of the fillers to be used can be selected appropriately. From the viewpoints of, for example, handling ability and mechanical strength of the resultant composition, the mean particle size of the organic fillers is preferably 0.001 to 50 μm and more preferably 0.001 to 10 μm.

Examples of materials for the inorganic fillers include quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. Similarly, these can be used independently or two or more of them can be used in mixture. The shapes of the inorganic fillers are not particularly limited and particle sizes of the fillers to be used can be selected appropriately. From the viewpoints of, for example, handling ability and mechanical strength of the resultant composition, the mean particle size of the inorganic fillers is preferably 0.001 to 50 μm and more preferably 0.001 to 10 μm.

Examples of the shapes of the inorganic fillers include amorphous fillers and spherical fillers. From the viewpoint of improving the mechanical strength of a composition, it is preferable that spherical fillers be used as the inorganic fillers. Furthermore, in the case of using the spherical fillers, when a polymerizable composition of the present invention is used as a dental composite resin, there also is an advantage that a composition resin with excellent surface smoothness is obtained. In this case, the spherical fillers are fillers in which when a photograph thereof is taken with a scanning electron microscope (hereinafter abbreviated as SEM), particles observed within a unit field of view are rounded and the mean uniformity obtained by dividing the particle size in the direction orthogonal to the maximum diameter by the maximum diameter is at least 0.6. The mean particle size of the spherical fillers is preferably 0.1 to 5 μm. When the mean particle size is less than 0.1 μm, the filling rate of the spherical fillers in the composition decreases and thereby the mechanical strength may be reduced. On the other hand, when the mean particle size exceeds 5 μm, the surface areas of the spherical fillers are reduced and a cured product with high mechanical strength may not be obtained.

The inorganic fillers may be used after the surfaces thereof are treated beforehand with a known surface-treating agent such as a silane coupling agent in order to adjust fluidity of the composition as required. Examples of such a surface-treating agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite fillers used in the present invention can be obtained as follows. That is, a monomer compound is added to the aforementioned inorganic filler beforehand, this is made into a paste and is then polymerized, and thereafter this is crushed. The organic-inorganic composite filler that can be used is, for example, a TMPT filler (obtained by mixing trimethylolpropane methacrylate with a silica filler, polymerizing it, and then crushing it). The shape of the organic-inorganic composite filler is not particularly limited, and the particle size of the filler to be used can be selected appropriately. From the viewpoints of, for example, handling ability and mechanical strength of the resultant composition, the mean particle size of the organic-inorganic composite filler is preferably 0.001 to 50 pm and more preferably 0.001 to 10 μm.

The amount of the filler (G) to be added in the present invention is not particularly limited, but it is preferable that 1 to 2000 parts by mass of filler (G) be contained with respect to 100 parts by mass of the whole amount of polymerizable monomer components. The preferable amount of filler (G) to be added varies considerably depending on the embodiment to be employed. Accordingly, preferable amounts of the filler (G) to be added according to the respective embodiments are indicated together with description of specific embodiments of the polymerizable composition of the present invention described later.

Preferably, the polymerizable composition of the present invention contains a solvent (H) depending on the specific embodiment. Examples of the solvent include water (I), an organic solvent (J), and a mixed solvent thereof.

When the polymerizable composition of the present invention contains water (I), it exhibits both excellent bond strength and excellent bond durability. Preferably, the content of water (I) is 6 to 2000 parts by mass with respect to 100 parts by mass of the whole amount of polymerizable monomer components. When the content of water (I) is less than 6 parts by mass, the monomer does not penetrate sufficiently into a collagen layer and the bond strength is reduced. On the other hand, when the content of water (I) exceeds 2000 parts by mass, the polymerizability of the monomer is deteriorated and both the bond strength and bond durability are reduced. The content of water (I) is more preferably at least 7 parts by mass and further preferably at least 10 parts by mass. Furthermore, the content of water (I) is more preferably 1500 parts by mass or less. Preferably, water (I) is free of impurities that have adverse effects, and distilled water or ion exchanged water is preferable.

Examples of the organic solvent (J) include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Particularly, when both safety to biological bodies and easy removal based on volatility are taken into consideration, the organic solvent (J) is preferably a water-soluble organic solvent. Specifically, ethanol, 2-propanol, 2-methyl-2-propanol, acetone, and tetrahydrofuran are used preferably. The content of organic solvent (J) is not particularly limited and the organic solvent (J) may not need to be added depending on the embodiment. In an embodiment using the organic solvent, it is preferable that 1 to 2000 parts by mass of organic solvent (J) be contained with respect to 100 parts by mass of the whole amount of polymerizable monomer components. The preferable amount of the organic solvent (J) to be added varies considerably depending on the embodiment in which it is used. Therefore, preferable amounts of organic solvents (J) to be added according to respective embodiments are indicated together with description of specific embodiments of the polymerizable composition of the present invention described later.

In addition, for example, a pH adjuster, polymerization inhibitor, ultraviolet absorbent, thickening agent, colorant, antibacterial agent, and flavor may be added to the polymerizable composition of the present invention within a range that does not inhibit the effects of the present invention.

The polymerizable composition of the present invention is used suitably as a dental composition. This dental composition can be used for dental materials such as a primer, bonding material, cement (resin cement, glass ionomer cement, and resin-reinforced glass ionomer cement), composite resin, pit and fissure sealant, and denture base resin, and particularly, it is used suitably as a primer, bonding material, cement, or composite resin.

With respect to a dental material, generally, a dental adhesive is used when a lost part of a tooth is filled or covered with a restorative material. Typically, the dental adhesive is allowed to act on dentin. In this case, when such a dental adhesive is allowed to act on dentin, it is important for the dental adhesive to have an decalcifying effect that allows a dentin surface to be dissolved with an acidic component, a penetration effect that allows a monomer component to penetrate into a collagen layer of the dentin, and a curing effect that allows the monomer component thus penetrated to solidify to form a hybrid layer (hereinafter also referred to as a "resin-impregnated layer") with collagen. Generally, a bonding system in which these three steps, "decalcifying", "penetration", and "curing", are performed separately is referred to as a "three-step bonding system". Basically, a product used for the penetration step is a primer, and a product used for the curing step is a bonding material.

Recently, in order to simplify the operation process, a product that allows the decalcifying step and the penetration step to be performed together in one step has been developed and has been used practically. The product is referred to as a "self-etching primer". Generally, the bonding system using a self-etching primer and a bonding material is referred to as a "two-step bonding system". The compound (A) used in the present invention has at least three hydroxyl groups and has high hydrophilicity. Therefore, it easily penetrates into a collagen layer of dentin. Accordingly, a polymerizable composition of the present invention containing a compound (A) can be used as a dental primer and also can be used as a dental self-etching primer.

Preferably, the primer containing a polymerizable composition of the present invention is a composition containing a compound (A), polymerizable monomer (C) having an acidic group, and solvent (H). Furthermore, an embodiment containing a polymerization accelerator (F) also is used preferably. The amounts of the above-mentioned (A) and (C) to be added are preferably 1 to 99 parts by mass of (A) and 1 to 99 parts by mass of (C), more preferably 5 to 98 parts by mass of (A) and 2 to 95 parts by mass of (C), and further preferably 10 to 97 parts by mass of (A) and 3 to 90 parts by mass of (C), in 100 parts by mass of the whole amount of polymerizable monomer components.

Furthermore, when penetrability of a primer composition into a tooth structure (particularly dentin) is considered important, it is preferable that further a polymerizable monomer (B) having one polymerizable group and at least one hydroxyl group be contained. When the primer composition contains (A), (B), and (C), the amounts of respective components to be added are preferably 1 to 98 parts by mass of (A), 1 to 90 parts by mass of (B), and 1 to 90 parts by mass of (C), more preferably 3 to 90 parts by mass of (A), 5 to 80 parts by mass of (B), and 2 to 80 parts by mass of (C), and further preferably 10 to 80 parts by mass of (A), 7 to 70 parts by mass of (B), and 3 to 60 parts by mass of (C), in 100 parts by mass of the whole amount of polymerizable monomer components.

When particularly the strength of the cured product of a primer containing a polymerizable composition of the present invention is intended to be improved, a crosslinkable polymerizable monomer (D) further may be added. When consideration is given to penetrability into a tooth structure (particularly dentin), the above-mentioned (D) is preferably an aliphatic compound-based bifunctional polymerizable monomer, more preferably ethylene glycol di(meth)acrylate, diethylene glycol di(meth)acrylate, triethylene glycol di(meth)acrylate, or 1,2-bis(3-methacryloyloxy-2-hydroxypropoxy)ethane, and further preferably triethylene glycol di(meth)acrylate, or 1,2-bis(3-methacryloyloxy-2-hydroxypropoxy)ethane. The amount of the above-mentioned (D) to be added is preferably 0 to 30 parts by mass, more preferably 1 to 25 parts by mass, and further preferably 3 to 20 parts by mass, in 100 parts by mass of the whole amount of polymerizable monomer components.

Furthermore, the amount of the polymerization initiator (E) to be contained is preferably 0.001 to 30 parts by mass, more preferably 0.05 to 20 parts by mass, and further preferably 0.1 to 10 parts by mass, with respect to 100 parts by mass of the whole amount of polymerizable monomer components. In the primer containing a polymerizable composition of the present invention, the use of the polymerization initiator (E) and the polymerization accelerator (F) in combination also is a preferable embodiment. Amines are used preferably as the polymerization accelerator (F). In this case, the amounts of (E) and (F) to be contained are preferably 0.001 to 30 parts by mass of (E) and 0.001 to 30 parts by mass of (F), more preferably 0.05 to 20 parts by mass of (E) and 0.05 to 20 parts by mass of (F), and further preferably 0.1 to 10 parts by mass of (E) and 0.1 to 10 parts by mass of (F), with respect to 100 parts by mass of the whole amount of polymerizable monomer components.

In the primer containing a polymerizable composition of the present invention, since the compound (A) has at least three hydroxyl groups in the molecule, hydrophilicity of the polymerizable composition of the present invention can be improved and thereby penetrability into a collagen layer of dentin can be improved. Furthermore, it is preferable that the solvent (H) be used in the form of a mixed solvent of water (I) and an organic solvent (J). The amount of water (I) to be contained in the mixed solvent is not particularly limited but is preferably at least 10 mass %, more preferably at least 30 mass %, and further preferably at least 50 mass %. Moreover, the organic solvent (J) may not need to be added depending on the embodiment. The amount of the aforementioned solvent (H) to be added is preferably 5 to 4000 parts by mass, preferably 10 to 3000 parts by mass, and further preferably 15 to 2000 parts by mass, with respect to 100 parts by mass of the whole amount of polymerizable monomer components. Furthermore, when the solvent (H) is used in the form of a mixed solvent of water (I) and the organic solvent (J), the amounts of the aforementioned (I) and (J) to be added are preferably 4 to 2000 parts by mass of (I) and 1 to 2000 parts by mass of (J), more preferably 8 to 1500 parts by mass of (I) and 2 to 1500 parts by mass of (J), and further preferably 12 to 1000 parts by mass of (I) and 3 to 1000 parts by mass of (J), with respect to 100 parts by mass of the whole amount of polymerizable monomer components.

The polymerizable composition of the present invention is used preferably as a bonding material. Preferably, the bonding material in the aforementioned "two-step bonding system" is a composition containing the aforementioned compound (A), polymerization initiator (E), and filler (G). More preferably, such a composition further contains a polymerizable monomer (B) having one polymerizable group and at least one hydroxyl group and/or crosslinkable polymerizable monomer (D). Furthermore, an embodiment containing a polymerization accelerator (F) also is used preferably. The amounts of respective components to be added are preferably 1 to 100 parts by mass of (A), 0 to 90 parts by mass of (B), and 0 to 90 parts by mass of (D), and more preferably 2 to 96 parts by mass of (A), 1 to 80 parts by mass of (B), and 1 to 80 parts by mass of (D), in 100 parts by mass of the whole amount of polymerizable monomer components. As in the case of the above-mentioned (A) used in the present invention, the use of a compound having at least two polymerizable groups allows a cured product to have increased mechanical strength. From such a viewpoint, the aforementioned (D) is more preferably a polymerizable monomer having at least two polymerizable groups, and from a viewpoint of obtaining a cured product with particularly high strength, it is further preferable that the aforementioned (D) contain an aromatic compound-based bifunctional polymerizable monomer. The use of an aliphatic bifunctional polymerizable monomer and aromatic compound-based bifunctional polymerizable monomer in combination as the aforementioned (D) also is a preferable embodiment.

Furthermore, the amount of (E) to be contained is preferably 0.001 to 30 parts by mass, more preferably 0.05 to 20 parts by mass, and further preferably 0.1 to 15 parts by mass, with respect to 100 parts by mass of the whole amount of polymerizable monomer components. Furthermore, the use of the polymerization initiator (E) and the polymerization accelerator (F) in combination also is a preferable embodiment, and preferably, amines are used as the polymerization accelerator (F). In this case, the amounts of (E) and (F) to be contained are preferably 0.001 to 30 parts by mass of (E) and 0.001 to 30 parts by mass of (F), more preferably 0.05 to 20 parts by mass of (E) and 0.05 to 20 parts by mass of (F), and further preferably 0.1 to 10 parts by mass of (E) and 0.1 to 10 parts by mass of (F), with respect to 100 parts by mass of the whole amount of polymerizable monomer components. Moreover, the amount of filler (G) to be added is preferably 1 to 20 parts by mass, more preferably 2 to 17 parts by mass, and further preferably 3 to 15 parts by mass, with respect to 100 parts by mass of the whole amount of polymerizable monomer components.

Recently, since there are demands for further simplification in operations, products that allow three steps of "decalcifying", "penetration", and "curing" to be performed together in one step also have been developed and are referred to as "one-step bonding systems". Two typical products of the bonding material used in such a one-step bonding system are a bonding material in which two separate liquids of liquid A and liquid B are mixed together immediately before use and a bonding material that is provided in the form of one liquid from the beginning and that is a so-called one-component one-step bonding system. Among these, the one-component type product further simplifies the process and therefore has a greater advantage in use. When a polymerizable composition of the present invention is used as the bonding material of the aforementioned one-component one-step bonding system, the composition is preferably a composition containing a compound (A), polymerizable monomer (C) having an acidic group, polymerization initiator (E), filler (G), and solvent (H), and further preferably, such a composition further contains a crosslinkable polymerizable monomer (D). The amounts of respective components to be added are preferably 1 to 98 parts by mass of (A), 1 to 90 parts by mass (C), and 0 to 90 parts by mass of (D), more preferably 2 to 94 parts by mass of (A), 2 to 80 parts by mass of (C), and 2 to 80 parts by mass of (D), and further preferably 7 to 90 parts by mass of (A), 3 to 70 parts by mass of (C), and 7 to 70 parts by mass of (D), in 100 parts by mass of the whole amount of polymerizable monomer components. In the one-component one-step bonding system, since the "penetration" and "curing" are performed at one time, the use of a polymerizable monomer having at least three hydroxyl groups and at least two polymerizable groups like the aforementioned (A) is of great significance.

In the one-component one-step bonding system, when penetrability into a tooth structure (particularly dentin) is considered important, it is preferable that a polymerizable monomer (B) having one polymerizable group and at least one hydroxyl group further be contained. When the one-component one-step bonding system contains (A), (B), (C), and (D), the amounts of respective components to be added are preferably 1 to 95 parts by mass of (A), 1 to 95 parts by mass of (B), 1 to 95 parts by mass of (C), and 3 to 97 parts by mass of (D), more preferably 3 to 90 parts by mass of (A), 3 to 80 parts by mass of (B), 2 to 80 parts by mass of (C), and 5 to 80 parts by mass of (D), and further preferably 5 to 80 parts by mass of (A), 5 to 70 parts by mass of (B), 3 to 60 parts by mass of (C), and 12 to 70 parts by mass of (D), in 100 parts by mass of the whole amount of polymerizable monomer components.

The amount of (E) to be contained is preferably 0.001 to 30 parts by mass, more preferably 0.05 to 20 parts by mass, and further preferably 0.1 to 15 parts by mass, with respect to 100 parts by mass of the whole amount of polymerizable monomer components. Furthermore, the use of the polymerization initiator (E) and the polymerization accelerator (F) in combination also is a preferable embodiment, and preferably, amines are used as the polymerization accelerator (F). In this case, the amounts of (E) and (F) to be contained are preferably 0.001 to 30 parts by mass of (E) and 0.001 to 30 parts by mass of (F), more preferably 0.05 to 20 parts by mass of (E) and 0.05 to 20 parts by mass of (F), and further preferably 0.1 to 10 parts by mass of (E) and 0.1 to 10 parts by mass of (F), with respect to 100 parts by mass of the whole amount of polymerizable monomer components. Furthermore, the amount of filler (G) to be added is preferably 1 to 20 parts by mass, more preferably 1.5 to 15 parts by mass, and further preferably 2 to 10 parts by mass, with respect to 100 parts by mass of the whole amount of polymerizable monomer components.

The amount of solvent (H) to be added is preferably 6 to 4000 parts by mass, more preferably 12 to 3000 parts by mass, and further preferably 15 to 2000 parts by mass, with respect to 100 parts by mass of the whole amount of polymerizable monomer components. The one-component one-step bonding system needs to perform all the processes of decalcifying, penetration, and curing with one liquid in one step. Therefore, from the viewpoint that penetrability is considered important, it is preferable that water (I) be contained as the solvent (H). On the other hand, from the viewpoint that curability is considered important, it is preferable that the bonding system contain a suitable amount of crosslinkable polymerizable monomer (D). From the viewpoints of increasing the solubility of the aforementioned (D) and obtaining a uniform solution, it is preferable that an organic solvent (J) be contained as the aforementioned solvent (H). A more preferable embodiment is the use of the solvent (H) in the form of a mixed solvent of water (I) and an organic solvent (J). In such an embodiment, the amounts of the aforementioned (I) and (J) to be added are preferably 2 to 2000 parts by mass of (I) and 4 to 2000 parts by mass of (J), more preferably 4 to 1500 parts by mass of (I) and 8 to 1500 parts by mass of (J), and further preferably 5 to 1000 parts by mass of (I) and 10 to 1000 parts by mass of (J), with respect to 100 parts by mass of the whole amount of polymerizable monomer components.

The polymerizable composition of the present invention is used preferably as composite resin. When the polymerizable composition of the present invention is used as composite resin, the composition is preferably one containing a compound (A), crosslinkable polymerizable monomer (D), polymerization initiator (E), and filler (G). Generally, the composite resin is used in the form of filling a cavity after the cavity is formed by cutting a site of caries incidence. Thereafter, generally, the composite resin filling the cavity is cured through photopolymerization. Therefore, the use of a photopolymerization initiator as the aforementioned (E) is preferable. Furthermore, since the composite resin that has filled the cavity and that has been cured as described above is subjected to occlusal pressure inside an oral cavity, high mechanical strength is required. Accordingly, the content of the filler (G) in the composition is preferably 30 to 2000 parts by mass and more preferably 50 to 1500 parts by mass, with respect to 100 parts by mass of the whole amount of polymerizable monomer components. When the content of the filler (G) is less than 30 parts by mass, mechanical strength of the cured product may be insufficient. On the other hand, when the content of the filler (G) exceeds 2000 parts by mass, it may become difficult to disperse the filler (G) uniformly throughout the whole amount of polymerizable monomer components, which may result in a composition that is insufficient in mechanical strength and handling ability. The amounts of respective components to be added are preferably 1 to 99 parts by mass of (A) and 1 to 99 parts by mass of (D), more preferably 5 to 95 parts by mass of (A) and 5 to 95 parts by mass of (D), and further preferably 10 to 90 parts by mass of (A) and 10 to 90 parts by mass of (D), in 100 parts by mass of the whole amount of polymerizable monomer components. Furthermore, the amount of (E) to be contained is preferably 0.001 to 30 parts by mass, more preferably 0.05 to 20 parts by mass, and further preferably 0.1 to 15 parts by mass, with respect to 100 parts by mass of the whole amount of polymerizable monomer components. The combined use of the polymerization initiator (E) and the polymerization accelerator (F) also is a preferable embodiment, and preferably, amines are used as the polymerization accelerator (F). In this case, the amounts of (E) and (F) to be contained are preferably 0.001 to 30 parts by mass of (E) and 0.001 to 30 parts by mass of (F), more preferably 0.05 to 20 parts by mass of (E) and 0.05 to 20 parts by mass of (F), and further preferably 0.1 to 10 parts by mass of (E) and 0.1 to 10 parts by mass of (F), with respect to 100 parts by mass of the whole amount of polymerizable monomer components.

Since the compound (A) of the present invention has both excellent curability and penetrability into a tooth structure, it is preferable that it be used particularly as a self-adhesive composite resin among composite resins. When the polymerizable composition of the present invention is used as a self-adhesive composite resin, it is preferable that the composition contain a compound (A), polymerizable monomer (C) having an acidic group, crosslinkable polymerizable monomer (D), polymerization initiator (E), and filler (G). The amounts of respective components to be added are preferably 1 to 95 parts by mass of (A), 1 to 95 parts by mass of (C), and 4 to 98 parts by mass of (D), more preferably 5 to 80 parts by mass of (A), 2 to 80 parts by mass of (C), and 10 to 93 parts by mass of (D), and further preferably 10 to 80 parts by mass of (A), 3 to 80 parts by mass of (C), and 4 to 87 parts by mass of (D), in 100 parts by mass of the whole amount of polymerizable monomer components. Furthermore, when the penetrability into a tooth structure (particularly dentin) is considered important, it is preferable that the composition further contain a polymerizable monomer (B) having one polymerizable group and at least one hydroxyl group. When the self-adhesive composite resin contains (A), (B), (C), and (D), the amounts of respective components to be added are preferably 1 to 95 parts by mass of (A), 1 to 95 parts by mass of (B), 1 to 95 parts by mass of (C), and 3 to 97 parts by mass of (D), more preferably 3 to 90 parts by mass of (A), 3 to 80 parts by mass of (B), 2 to 80 parts by mass of (C), and 5 to 80 parts by mass of (D), and further preferably 5 to 80 parts by mass of (A), 5 to 70 parts by mass of (B), 3 to 60 parts by mass of (C), and 12 to 70 parts by mass of (D), in 100 parts by mass of the whole amount of polymerizable monomer components. With respect to the amounts of polymerization initiator (E) and filler (G) to be added, the same amounts as those used in the aforementioned general composite resin can be employed. Furthermore, in the same manner as in the case of the aforementioned general composite resin, the combined use of the polymerization initiator (E) and the polymerization accelerator (F) also is a preferable embodiment. The amounts of the aforementioned (E) and (F) to be added are as described above. Moreover, when particularly the penetrability into a tooth structure is considered important, it also is possible to add a solvent (H), and it is further preferable that the solvent (H) contain water (I). The amount of solvent (H) to be added is preferably 0 to 15 parts by mass and more preferably 1 to 10 parts by mass, with respect to 100 parts by mass of the whole amount of polymerizable monomer components.

Furthermore, the use of a polymerizable composition of the present invention as a dental cement also is one of preferable embodiments. Examples of preferable cements include a resin cement, glass ionomer cement, and resin-reinforced glass ionomer cement. When the polymerizable composition of the present invention is used as a resin cement, the composition is preferably one containing a compound (A), crosslinkable polymerizable monomer (D), polymerization initiator (E), polymerization accelerator (F), filler (G), and water (I) to serve as a solvent (H). Such a composition further can contain a polymerizable monomer (C) having an acidic group. The dental cement is used suitably as, for example, a luting material that is used in fixing a metal or ceramic dental crown restorative material, which is referred to as an "inlay" or "crown", to a tooth. As in the case of the aforementioned (A) used in the present invention, when at least two polymerizable groups are included, the resultant cured product has increased mechanical strength and can withstand, for example, occlusal pressure. From such a viewpoint, it is more preferable that the aforementioned (D) be a polymerizable monomer having at least two polymerizable groups. Furthermore, in the case of the form of usage as described above, since many of the dental crown restorative materials have optical opacity, it is not easy to cure the cement by only photopolymerization. Therefore, it is preferable that a chemical polymerization initiator be used as the aforementioned (E). Furthermore, when polymerization is performed by using a chemical polymerization initiator, in order to improve the reactivity thereof, the use of amines and/or sulfinic acid and salt thereof as the aforementioned (F) is preferable and the simultaneous use of amines and sulfinic acid and salt thereof is more preferable. The filler (G) used is not particularly limited.

When the cement is intended to be provided with a property of sustained-release of fluoride, it is preferable that at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass be used as the filler (G), and it is more preferable that fluoroaluminosilicate glass and/or barium fluoroaluminosilicate glass be used as the filler (G). On the other hand, when the cement is intended to be provided with radiopacity, it is preferable that at least one selected from the group consisting of barium glass, strontium glass, barium boroaluminosilicate glass, strontium boroaluminosilicate glass, strontium fluoroaluminosilicate glass, and barium fluoroaluminosilicate glass be used as the filler (G), and it is more preferable that barium glass and/or barium fluoroaluminosilicate glass be used as the filler (G).

When a chemical polymerization initiator is used, from the viewpoint of storage stability, it is preferable that the aforementioned (E) and (F) be stored in separate containers, respectively. That is, in a preferred embodiment, the resin cement is used in the form of a two component type. In a more preferred embodiment, the resin cement is used in the form of two paste type. Preferably, the respective pastes are stored while being separated from each other, the two pastes are mixed together immediately before use, and thereby chemical polymerization is allowed to proceed to cure the mixture. The aforementioned pastes each are prepared by mixing a liquid component of, for example, polymerizable monomer with a filler (G) (powder) together. Furthermore, when sulfinic acid and salt thereof are used as the aforementioned (F), from the viewpoint of storage stability, it is preferable that the aforementioned (C) and (F) be stored in separate containers, respectively. Suppose that the aforementioned two pastes are referred to as a paste A and a paste B, respectively, an embodiment in which the paste A contains (A), (C), (E), and (G), and the paste B contains (A), (F), and (G) is used particularly suitably.

When the polymerizable composition of the present invention is used as a dental cement, the amounts of respective components to be added are not particularly limited. However, in 100 parts by mass of the whole amount of polymerizable monomer components, the composition contains preferably 1 to 98 parts by mass of (A), 1 to 90 parts by mass of (C), and 1 to 90 parts by mass of (D), and more preferably 2 to 96 parts by mass of (A), 2 to 80 parts by mass of (C), and 2 to 80 parts by mass of (D). When consideration is given to obtaining a suitable setting time, the amounts of the aforementioned (E) and (F) to be added are preferably 0.001 to 30 parts by mass of (E) and 0.001 to 30 parts by mass of (F), and more preferably 0.05 to 20 parts by mass of (E) and 0.05 to 20 parts by mass of (F), with respect to 100 parts by mass of the whole amount of polymerizable monomer components.

Furthermore, with respect to 100 parts by mass of the whole amount of polymerizable monomer components, the content of (G) is preferably 30 to 2000 parts by mass and more preferably 50 to 1500 parts by mass. When the content of (G) is less than 30 parts by mass, mechanical strength of the cured product may be insufficient. On the other hand, in the case where the content of (G) exceeds 2000 parts by mass, when the resin cement is used as a two-paste-type cement, which is a preferred embodiment, the pastes lack fluidity, which makes it difficult to carry out sufficient mixing, and therefore the cured product may have reduced strength.

The polymerizable composition of the present invention is used preferably as a glass ionomer cement and more preferably as a resin-reinforced glass ionomer cement. The glass ionomer cement is typically one in which an inorganic filler such as fluoroaluminosilicate glass and polyalkenoic acid such as polyacrylic acid are reacted with each other through an acid-base reaction to be cured. Conceivably, the polyacrylic acid interacts with calcium contained in hydroxyapatite composing a tooth structure and thereby a bonding function is exhibited. When a polymerizable composition of the present invention is used as a glass ionomer cement, particularly preferably as a resin-reinforced glass ionomer cement, the composition is preferably one containing (A), (E), (F), (G), (H), and polyalkenoic acid, and more preferably one containing (A), (D), (E), (F), (G), (H), and polyalkenoic acid, one containing (A), (B), (E), (F), (G), (H), and polyalkenoic acid, or one containing (A), (B), (D), (E), (F), (G), (H), and polyalkenoic acid. Such compositions further can contain (C).

The polymerizable monomer (B) having one polymerizable group and at least one hydroxyl group to be used is not particularly limited. As described later, from the viewpoint that an acid-base reaction is allowed to proceed smoothly, it is preferable that the solvent (H) contain water (I). Therefore, from the viewpoints of maintaining the uniformity of the composition and obtaining consistent performance, it is more preferable that a monomer with high affinity for water (I) be used as the aforementioned (B). Such a monomer with high affinity for water (I) is preferably 2-hydroxyethyl(meth)acrylate, 3-hydroxypropyl(meth)acrylate, glycerol mono(meth)acrylate, or erythritol mono(meth)acrylate and particularly preferably 2-hydroxyethylmethacrylate.

The crosslinkable polymerizable monomer (D) to be used is not particularly limited, but as described above, the use of a monomer with high affinity for water (I) as the aforementioned (D) is more preferable from the viewpoints of maintaining the uniformity of the composition and obtaining consistent performance. In terms of a balance between such affinity for water (I) and the mechanical strength of the cured product, the aforementioned (D) is preferably an aliphatic compound-based bifunctional polymerizable monomer and more preferably triethylene glycol di(meth)acrylate, polyethylene glycol di(meth)acrylate, neopentyl glycol di(meth)acrylate, 1,2-bis(3-methacryloyloxy-2-hydroxypropoxy) ethane, or 2,2,4-trimethylhexamethylenebis(2-carbamoyloxyethyl) dimethacrylate (commonly known as "UDMA").

The aforementioned polyalkenoic acid is a polymer of unsaturated monocarboxylic acid or unsaturated dicarboxylic acid. Specific examples of the polyalkenoic acid include homopolymers of, for example, acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, and utraconic acid, or copolymers of these unsaturated carboxylic acids and monomers copolymerizable therewith. In the case of the copolymers, the ratio of the unsaturated carboxylic acid unit is preferably at least 50 mol % with respect to the total structure unit. An ethylenically unsaturated polymerizable monomer is preferable as the copolymerizable monomer, and examples thereof include styrene, acrylamide, acrylonitrile, methyl methacrylate, acrylic acid salts, vinyl chloride, allyl chloride, vinyl acetate, and 1,1,6-trimethylhexamethylene dimethacrylate ester. Among those polyalkenoic acids, a homopolymer or copolymer of acrylic acid or maleic acid is preferable. When these polyalkenoic acids have a weight-average molecular weight of less than 5,000, the cured product of the dental cement composition may have reduced strength and poor durability. On the other hand, when it has a weight-average molecular weight exceeding 40,000, it may have high consistency during mixing of the dental cement composition and therefore may have lower operability. Accordingly, a preferable weight-average molecular weight of the polyalkenoic acid is 5,000 to 40,000.

From the viewpoints of curability in the acid-base reaction and the property of sustained-release of fluoride of the composition, the filler (G) to be used is preferably at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass, and more preferably fluoroaluminosilicate glass and/or barium fluoroaluminosilicate glass.

Furthermore, the solvent (H) to be used is not particularly limited. However, from the viewpoint that an acid-base reaction is allowed to proceed smoothly, it is preferable that the solvent (H) contain water (I). When a mixed solvent of water (I) and an organic solvent (J) is used as the solvent (H), the content of water (I) in the mixed solvent is preferably at least 50 mass %, more preferably at least 70 mass %, and further preferably at least 90 mass %. In an embodiment in which particularly progress of the acid-base reaction is considered important, it is particularly preferable that the solvent (H) consist substantially of water (I) alone.

When a polymerizable composition of the present invention is used as a glass ionomer cement, particularly preferably as a resin-reinforced glass ionomer cement, the amounts of respective components to be added are not particularly limited. When the polymerizable composition contains (A) and (B), it contains preferably 1 to 99 parts by mass of (A), 1 to 99 parts by mass of (B), and 0 to 50 parts by mass of (C), and more preferably 2 to 95 parts by mass of (A), 5 to 98 parts by mass of (B), and 0 to 30 parts by mass of (C), in 100 parts by mass of the whole amount of polymerizable monomer components. When the polymerizable composition contains (A) and (D), it contains preferably 1 to 99 parts by mass of (A), 1 to 99 parts by mass of (D), and 0 to 50 parts by mass of (C), and more preferably 2 to 95 parts by mass of (A), 5 to 98 parts by mass of (D), and 0 to 30 parts by mass of (C), in 100 parts by mass of the whole amount of polymerizable monomer components. Furthermore, when the polymerizable composition contains (A), (B), and (D), it contains preferably 1 to 98 parts by mass of (A), 1 to 98 parts by mass of (B), 1 to 98 parts by mass of (D), and 0 to 50 parts by mass of (C), and more preferably 2 to 90 parts by mass of (A), 5 to 93 parts by mass of (B), 5 to 93 parts by mass of (D), and 0 to 30 parts by mass of (C), in 100 parts by mass of the whole amount of polymerizable monomer components.

When consideration is given to obtaining a suitable setting time, the amounts of the aforementioned (E) and (F) to be added are preferably 0.001 to 30 parts by mass of (E) and 0.001 to 30 parts by mass of (F), and more preferably 0.05 to 20 parts by mass of (E) and 0.05 to 20 parts by mass of (F), with respect to 100 parts by mass of the whole amount of polymerizable monomer components. Moreover, the content of (G) is preferably 30 to 2000 parts by mass and more preferably 50 to 1500 parts by mass, with respect to 100 parts by mass of the whole amount of polymerizable monomer components. When the content of (G) is less than 30 parts by mass, mechanical strength of the cured product may be insufficient. On the other hand, when the content of (G) exceeds 2000 parts by mass, the composition paste has lower fluidity, which makes sufficient mixing difficult, and therefore the acid-base reaction may not proceed smoothly. As a result, the cured product may have reduced strength.

With respect to 100 parts by mass of the whole amount of polymerizable monomer components, the content of solvent (H) is preferably 7 to 500 parts by mass, more preferably 10 to 300 parts by mass, and further preferably 20 to 100 parts by mass. When the solvent (H) is contained in such ranges, the acid-base reaction can proceed smoothly, and the resultant cured product has excellent mechanical strength and excellent adhesive properties to a tooth structure.

With respect to 100 parts by mass of the whole amount of polymerizable monomer components, the content of the aforementioned polyalkenoic acid is preferably 1 to 200 parts by mass, more preferably 5 to 100 parts by mass, and further preferably 10 to 50 parts by mass. When the polyalkenoic acid is contained in such ranges, curing through the acid-base reaction proceeds smoothly and decay of the resultant cured product inside an oral cavity by, for example, hydrolysis can be diminished.

As described above, since curing of a glass ionomer cement occurs through progress of an acid-base reaction, from the viewpoint of storage stability, it is preferable that a basic filler (G) and polyalkenoic acid be packed in separate containers and be used after being mixed immediately before use. The preferable types of products to be employed include a so-called powder-liquid type, but from the viewpoint of improving handling ability, the form of so-called two past-type glass ionomer cement containing two types of pastes is more preferable. In the case where the type of product is the two paste type, when the aforementioned two pastes are referred to as a paste A and a paste B, respectively, an embodiment is preferable in which the paste A contains (A), (E), (G), (H), and polyalkenoic acid and the paste B contains (B) and (G). Furthermore, an embodiment in which the paste A contains (A), (E), (G), (H), and polyalkenoic acid and the paste B contains (D) and (G) also is used preferably. In addition, an embodiment in which the paste A contains (D), (E), (G), and polyalkenoic acid and the paste B contains (A), (F), (G), and (H) also is used preferably. In this case, when particularly adhesive properties are considered important, it is preferable that the paste A further contain (C), and from the similar viewpoint, it also is preferable that the paste B further contain (B). In all of the embodiments, since the paste A contains polyalkenoic acid, it is preferable that at least one selected from the group consisting of fluoroaluminosilicate glass, calcium fluoroaluminosilicate glass, strontium fluoroaluminosilicate glass, barium fluoroaluminosilicate glass, and strontium calcium fluoroaluminosilicate glass be used as the filler (G) contained in the paste B, and it is more preferable that fluoroaluminosilicate glass and/or barium fluoroaluminosilicate glass be used as the filler (G). On the other hand, the filler (G) contained in the paste A to be used is preferably one that exhibits no reactivity with polyalkenoic acid, and particularly preferably quartz.

Hereinafter, the present invention is described in further detail using examples but is not limited thereto in any way.

EXAMPLE 1

Synthesis of Compound (A)

(1) Synthesis of 1,2:5,6-Di-O-isopropylidene-3,4-di-O-methacryloyl-D-mannitol

After 700 mL of anhydrous pyridine was added to a 2 L separable flask equipped with a condenser tube, 65 g of 1,2:5,6-Di-O-isopropylidene-D-mannitol (manufactured by Wako Pure Chemical Industries, Ltd.) was added into the flask gradually and was dissolved completely. An ice bath was set for the reaction system and the reaction system was cooled to 0° C. Subsequently, while the temperature of the reaction system was maintained around 0° C. and the reaction system was stirred, 60 g of methacryloyl chloride (manufactured by Wako Pure Chemical Industries, Ltd.) was dropped into the reaction system in a nitrogen atmosphere using a dropping funnel over approximately one hour. The dropping funnel was replaced by a glass stopper, and the reaction system was heated to 70° C. using an oil bath. This heating was continued for eight hours. After completion of heating, the oil bath was removed and the reaction system was then cooled to room temperature. Subsequently, the reaction system was poured into a beaker containing 1 L of ice water and thereby the reaction was stopped. After the reaction was stopped, extraction was performed five times using 1500 mL of diethyl ether. Thereafter, the resultant organic layer was subjected to vacuum concentration using an evaporator and thus an oily material was obtained. The oily material was purified using silica gel column chromatography (diluents: hexane:diethyl ether =7:3). After concentration, hexane was added and thereby recrystallization was carried out. Thus, a target compound was obtained. The yield amount was 36.3 g, and the yield rate was 37%.

$^1$H-NMR (400 MHz, CDCl$_3$, δ) 1.31 (s, 6H), 1.36 (s, 6H), 1.96 (s, 6H), 3.85-3.96 (m, 4H), 4.21-4.27 (m, 2H), 5.43 (dd, 2H), 5.64 (s, 2H), 6.15 (s, 2H) (ppm) $^{13}$C-NMR (100 MHz, CDCl$_3$, δ) 18.2, 25.1, 26.3, 65.5, 71.6, 74.7, 109.3, 126.6, 135.6, 166.0 (ppm)

(2) Synthesis of Polymerizable Monomer A-1 (3,4-di-O-methacryloyl-D-mannitol)

540 mL of acetic acid and 180 mL of water were added to a 2 L round-bottom flask. While the resultant acetic acid aqueous solution was stirred, 18 g of 1,2:5,6-Di-O-isopropylidene-3,4-di-O-methacryloyl-D-mannitol synthesized above was added gradually thereto and was dissolved completely. The solution thus prepared was stirred for 18 hours, with the temperature thereof being maintained at 25° C. After completion of stirring, the solution was subjected to vacuum concentration using an evaporator and thus an oily material was obtained. The oily material was purified using silica gel column chromatography (diluent: ethyl acetate 100%) and was concentrated. As a result, white crystals were precipitated. It was confirmed by NMR that these crystals were a target compound. The yield amount was 8.7 g and the yield rate was 60%.

$^1$H-NMR (400 MHz, CDCl$_3$OD, δ) 1.84 (s, 6H), 3.39 (dd, 2H), 3.51 (dd, 2H), 3.59-3.66 (m, 2H), 5.28 (d, 2H), 5.56 (s, 2H), 6.03 (s, 2H) (ppm)

$^{13}$C-NMR (100 MHz, CD$_3$OD, δ) 18.4, 64.2, 71.6, 73.1, 126.8, 137.4, 167.9 (ppm)

EXAMPLE 2

Application to Two-step Bonding System of Polymerizable Composition Containing Compound (A) (Two-component Bonding Material)

(1) Production of Primer Using Polymerizable Composition Containing Compound (A)

Primers using a polymerizable composition containing the compound (A) were produced. The compositions thereof are indicated in Table 1.

TABLE 1

| Components | | Ex. 2-1 | Ex. 2-2 | Ex. 2-3 | C. Ex. 2-1 |
|---|---|---|---|---|---|
| Compound (A) | A-1 | 40 | 20 | 40 | 0 |
| | GDMA | 0 | 0 | 0 | 40 |
| Polymerizable monomer (B) having one polymerizable group and at least one hydroxy group | HEMA | 0 | 20 | 0 | 0 |
| Polymerizable monomer (C) having acidic group | MDP | 15 | 15 | 15 | 15 |
| Polymerization initiator (E) | TMDPO | 0.5 | 0.5 | 0 | 0.5 |
| | CQ | 0 | 0 | 0.4 | 0 |
| Polymerization accelerator (F) | Amine 1 | 0 | 0 | 0.2 | 0 |
| Solvent (H) | Distilled water | 20 | 20 | 20 | 20 |
| | Ethanol | 20 | 20 | 20 | 20 |

TABLE 1-continued

| Components | Ex. 2-1 | Ex. 2-2 | Ex. 2-3 | C. Ex. 2-1 |
|---|---|---|---|---|
| Bond strength with respect to dentin (MPa) | 20.9 | 25.4 | 20.1 | 12.3 |

(The amounts of respective components added each are indicated in the unit of parts by mass.)
A-1: polymerizable monomer A-1 synthesized in Example 1
GDMA: glycerol dimethacrylate
HEMA: 2-hydroxyethylmethacrylate
MDP: 10-methacryloyloxydecyl dihydrogenphosphate
TMDPO: 2,4,6-trimethylbenzoyldiphenylphosphine oxide
CQ: camphorquinone
Amine 1: N,N-dimethylaminobenzoic acid n-butoxyethyl ester (2) Method of Evaluating Bonding to Bovine Teeth Dentin The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was controlled.

Each primer produced above was applied into the above-mentioned circular hole using a brush and was then allowed to stand for 20 seconds. Thereafter, the surface thereof was air-blown and thereby the primer thus applied was dried until it lost fluidity. Next, the bonding material having a composition indicated in Table 2 was applied over the tooth surface where the primer had been applied and dried. Subsequently, it was irradiated with light using a dental visible light unit "JET LITE 3000" (manufactured by J. Morita USA) for 20 seconds. Thus, the primer and bonding material that had been applied were cured.

A dental filling composite resin (manufactured by Kuraray Medical Inc., "CLEARFIL AP-X" (trade name, registered trademark)) was applied to the surface of the resultant cured product of the bonding material, and it was then covered with a mold release film (polyester). Next, slide glass was placed on the mold release film to press it, and thereby the surface of the applied composite resin was smoothed. Subsequently, the composite resin was irradiated with light for 20 seconds using the aforementioned unit "JET LITE 3000" through the mold release film. Thus, the composite resin was cured.

One end face (circular section) of a stainless-steel cylindrical rod (with a diameter of 7 mm and a length of 2.5 cm) was bonded to the surface of the resultant cured product of the dental filling composite resin using a commercially available dental resin cement (manufactured by Kuraray Medical Inc., "PANAVIA21" (trade name)). After bonding, this sample was allowed to stand still at room temperature for 30 minutes and was then immersed in distilled water. The resultant sample that had been immersed in distilled water was allowed to stand still for 24 hours inside a thermostat whose temperature was maintained at 37° C., so that a bonding test sample was produced. Five samples were produced in total.

TABLE 2

| Composition of Bonding Material-1 | |
|---|---|
| Components | Amount added (parts by mass) |
| HEMA | 40 |
| BisGMA | 40 |
| NPG | 20 |
| Photoinitiator (TMDPO) | 3 |
| Inorganic filler 1 | 5.5 |
| Inorganic filler 2 | 1.5 |

BisGMA: bisphenol A diglycidyl methacrylate
NPG: neopentyl glycol dimethacrylate
Inorganic filler 1: "R972" manufactured by Japan Aerosil Inc.
Inorganic filler 2: "Ar380" manufactured by Japan Aerosil Inc.
(The other abbreviations have the same meanings as described above.)

(3) Bonding Evaluation Test

The tensile bond strengths of the above-mentioned five bonding test samples were measured with a universal testing machine (manufactured by Shimadzu Corporation), with the crosshead speed being set at 2 mm/min, and the average value thereof was taken as tensile bond strength.

EXAMPLE 2-1

The above-mentioned bonding evaluation test was conducted to evaluate the bonding of the primer to bovine dentin, using, as the hydrophilic monomer to be added to the primer, "A-1" that corresponds to the compound (A).

EXAMPLE 2-2

The above-mentioned bonding evaluation test was conducted to evaluate the bonding of the primer to bovine dentin, using, as the hydrophilic monomer to be added to the primer, "A-1" that corresponds to the compound (A), and using, as the polymerizable monomer (B) having one polymerizable group and at least one hydroxyl group, HEMA.

EXAMPLE 2-3

The evaluation test was performed in the same way as in Example 2-1, except that the polymerization initiator used in Example 2-1 was changed as shown in Table 1 and that a polymerization accelerator was used.

COMPARATIVE EXAMPLE 2-1

The above-mentioned bonding evaluation test was conducted to evaluate the bonding of the primer to bovine enamel and dentin, using, as the hydrophilic monomer to be added to the primer, GDMA that does not correspond to the compound (A).

Table 1 shows the results. Table 1 reveals that the primers using the polymerizable composition containing the compound (A) of the present invention have excellent adhesive properties with respect to dentin.

(4) Production and Evaluation of Bonding Materials using Polymerizable Composition Containing Compound (A)

Subsequently, in order to use polymerizable compositions containing the compound (A) also for bonding materials, bonding materials using a polymerizable composition containing the compound (A) were produced. The compositions thereof are indicated in Table 3.

TABLE 3

Composition of Bonding Material-2

| Components | | Ex. 2-4 | Ex. 2-5 | Ex. 2-6 |
|---|---|---|---|---|
| Compound (A) | A-1 | 40 | 40 | 20 |
| Polymerizable monomer (B) having one polymerizable group and at least one hydroxyl group | HEMA | 0 | 0 | 20 |
| Crosslinkable polymerizable monomer (D) | BisGMA | 40 | 40 | 40 |
| | NPG | 20 | 20 | 20 |
| Polymerization initiator (E) | TMDPO | 3 | 0 | 3 |
| | CQ | 0 | 2 | 0 |
| Polymerization accelerator (F) | Amine 1 | 0 | 1 | 0 |
| Filler (G) | Inorganic filler 1 | 5.5 | 5.5 | 5.5 |

TABLE 3-continued

Composition of Bonding Material-2

| Components | | Ex. 2-4 | Ex. 2-5 | Ex. 2-6 |
|---|---|---|---|---|
| | Inorganic filler 2 | 1.5 | 1.5 | 1.5 |
| Bond strength with respect to dentin (MPa) | | 22.1 | 21.5 | 23.1 |

(The amounts of respective components added each are indicated in the unit of parts by mass, and the respective abbreviations have the same meanings as described above.)

EXAMPLE 2-4

The evaluation test was performed in the same way as in Example 2-1, except that the bonding material used in Example 2-1 was changed as shown in Table 3.

EXAMPLE 2-5

The evaluation test was performed in the same way as in Example 2-4, except that the polymerization initiator used in Example 2-4 was changed as shown in Table 3 and that a polymerization accelerator was used.

EXAMPLE 2-6

The evaluation test was performed in the same way as in Example 2-1, except that the bonding material used in Example 2-1 was changed as shown in Table 3.

Table 3 shows the results. The result of Example 2-1 shown in Table 1 and the results shown in Table 3 reveal that when the polymerizable composition containing the compound (A) of the present invention is used also for bonding materials, adhesive properties with respect to dentin can be improved further.

EXAMPLE 3

Application to One-step Bonding System of Polymerizable Composition Containing Compound (A) (One-component Bonding Material)

(1) Production of One-component Bonding Material

One-component bonding materials using a polymerizable composition containing the compound (A) were produced. The compositions thereof are indicated in Table 4.

TABLE 4

| Components | | Ex. 3-1 | Ex. 3-2 | Ex. 3-3 | C. Ex. 3-1 |
|---|---|---|---|---|---|
| Compound (A) | A-1 | 30 | 15 | 15 | 0 |
| | GDMA | 0 | 0 | 0 | 30 |
| Polymerizable monomer (B) having one polymerizable group and at least one hydroxyl group | HEMA | 0 | 15 | 15 | 0 |
| Polymerizable monomer (C) having acidic group | MDP | 10 | 10 | 10 | 10 |
| Crosslinkable polymerizable monomer (D) | BisGMA | 45 | 45 | 45 | 45 |
| Polymerization initiator (E) | TMDPO | 2 | 2 | 0 | 2 |
| | CQ | 0 | 0 | 2 | 0 |
| Polymerization accelerator (F) | Amine 1 | 0 | 0 | 1 | 0 |
| Filler (G) | Inorganic filler 1 | 5 | 5 | 5 | 5 |
| Solvent (H) | Distilled water | 10 | 10 | 10 | 10 |
| | Ethanol | 20 | 20 | 20 | 20 |
| Bond strength with respect to dentin (MPa) | After 24 hours | 12.1 | 16.1 | 15.1 | 8.2 |
| | After thermal cycles load | 14.6 | 18.7 | 17.9 | 7.1 |

(The amounts of respective components added each are indicated in the unit of parts by mass, and the respective abbreviations have the same meanings as described above.)

(2) Method of Evaluating Bonding to Bovine Teeth Dentin

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was controlled.

Each one-component bonding material produced above was applied into the above-mentioned circular hole using a brush and was then allowed to stand for 20 seconds. Thereafter, the surface thereof was air-blown and thereby the one-component bonding material thus applied was dried until it lost fluidity. Next, it was irradiated with light using a dental visible light unit "JET LITE 3000" (manufactured by J. Morita USA) for 20 seconds. Thus, the one-component bonding material that had been applied were cured.

A dental filling composite resin (manufactured by Kuraray Medical Inc., "CLEARFIL AP-X" (trade name, registered trademark)) was applied to the surface of the resultant cured product of the one-component bonding material, and it was then covered with a mold release film (polyester). Next, slide glass was placed on the mold release film to press it, and thereby the surface of the applied composite resin was smoothed. Subsequently, the composite resin was irradiated with light for 20 seconds using the aforementioned unit "JET LITE 3000" through the mold release film. Thus, the composite resin was cured.

One end face (circular section) of a stainless-steel cylindrical rod (with a diameter of 7 mm and a length of 2.5 cm) was bonded to the surface of the resultant cured product of the dental filling composite resin using a commercially available dental resin cement (manufactured by Kuraray Medical Inc., "PANAVIA21" (trade name)). After bonding, this sample was allowed to stand still at room temperature for 30 minutes and was then immersed in distilled water. The sample that had been immersed in distilled water was allowed to stand still for 24 hours inside a thermostat whose temperature was maintained at 37° C., so that a bonding test sample was produced. Five samples were produced in total.

(3) Bonding Evaluation Test (After 24 Hours)

The tensile bond strengths of the above-mentioned five bonding test samples were measured with a universal testing machine (manufactured by Shimadzu Corporation), with the crosshead speed being set at 2 mm/min, and the average value thereof was taken as tensile bond strength.

(4) Bonding Evaluation Test (After Thermal Cycles Load)

Five bonding test samples were produced in the same manner as the above-described method. In order to evaluate bond durability of the thus produced samples, bonding strength of each sample was measured, in accordance with the above-described method, after 4000 thermal cycles had been performed, with one cycle being a process for further immersing each sample in 4° C. cold water and 60° C. warm water alternately for one minute.

EXAMPLE 3-1

The above-mentioned bonding evaluation test was conducted to evaluate the bonding of the one-component bonding material to bovine dentin, using, as the hydrophilic monomer to be added to the one-component bonding material, "A-1" that corresponds to the compound (A).

EXAMPLE 3-2

The above-mentioned bonding evaluation test was conducted to evaluate the bonding of the one-component bonding material to bovine dentin, using, as the hydrophilic monomer to be added to the one-component bonding material, "A-1" that corresponds to the compound (A), and using, the polymerizable monomer (B) having one polymerizable group and at least one hydroxyl group, HEMA.

EXAMPLE 3-3

The evaluation test was performed in the same way as in Example 3-2, except that the polymerization initiator used in Example 3-2 was changed as shown in Table 2 and that a polymerization accelerator was used.

COMPARATIVE EXAMPLE 3-1

The above-mentioned bonding evaluation test was conducted to evaluate the bonding of the one-component bonding material to bovine dentin, using, as the hydrophilic monomer to be added to the one-component bonding material, GDMA that does not correspond to the compound (A).

Table 4 shows the results. Table 4 reveals that the bonding materials using the polymerizable composition containing the compound (A) of the present invention have excellent adhesive properties with respect to dentin.

INDUSTRIAL APPLICABILITY

The compound (A) of the present invention has a plurality of polymerizable groups and hydroxyl groups, and therefore is useful for applications that require the compound (A) to be curable and applications that require a polymer of the compound (A) to be hydrophilic. A polymerizable composition containing the polymerizable monomer can be used for various applications including dental applications. Particularly, this composition is suitable for dental materials such as a primer, bonding material, cement, and composite resin.

The invention claimed is:

1. A compound (A) represented by formula (1):

[Chemical Formula 1]

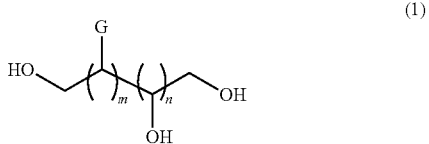

(1)

where G denotes a polymerizable group, m denotes an integer of 2 or more, n denotes an integer of 1 or more, and the sequence order of m units having a polymerizable group and n units having a hydroxyl group is arbitrary.

2. The compound (A) according to claim 1, wherein the polymerizable group is a group represented by formula (2), formula (3), or formula (4):

[Chemical Formula 2]

(2)

[Chemical Formula 3]

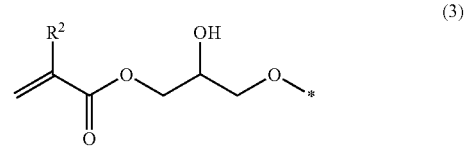

(3)

[Chemical Formula 4]

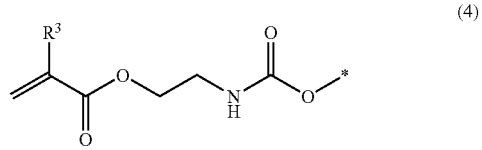

(4)

where $R^1$, $R^2$, and $R^3$ each denote a hydrogen atom or an aliphatic hydrocarbon group having 1 to 10 carbon atoms and "*" denotes a bond.

3. The compound (A) according to claim 2, wherein $R^1$ is a hydrogen atom or methyl group.

4. The compound (A) according to claim 1, wherein the compound (A) is a compound represented by formula (5):

[Chemical Formula 5]

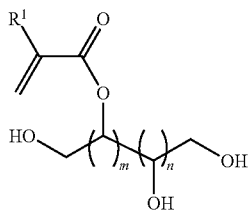

(5)

where $R^1$ denotes a hydrogen atom or an aliphatic hydrocarbon group having 1 to 10 carbon atoms, m denotes an integer of 2 or more, n denotes an integer of 1 or more, and the sequence order of m units having an ester group and n units having a hydroxyl group is arbitrary.

5. The compound (A) according to claim 1, wherein m is 2, and n is 2.

6. The compound (A) according to claim 1, wherein the compound (A) is a compound represented by formula (6):

[Chemical Formula 6]

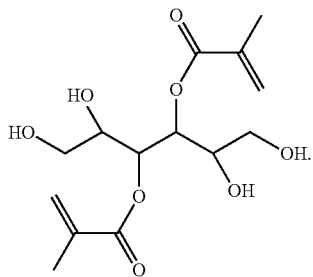

(6)

7. The compound (A) according to claim 1, wherein the compound (A) is a compound represented by formula (7):

[Chemical Formula 7]

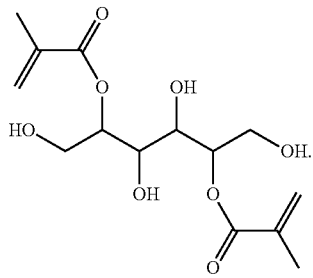

(7)

8. A polymerizable composition comprising, as a polymerizable monomer component, the compound (A) according to claim 1.

9. The polymerizable composition according to claim 8, further comprising, as a polymerizable monomer component, a polymerizable monomer (B) having one polymerizable group and at least one hydroxyl group.

10. The polymerizable composition according to claim 8, further comprising, as a polymerizable monomer component, a polymerizable monomer (C) having an acidic group.

11. The polymerizable composition according to claim 8, further comprising, as a polymerizable monomer component, a crosslinkable polymerizable monomer (D).

12. The polymerizable composition according to claim 8, comprising a polymerization initiator (E).

13. The polymerizable composition according to claim 8, comprising a polymerization accelerator (F).

14. The polymerizable composition according to claim 8, comprising a filler (G).

15. The polymerizable composition according to claim 8, comprising a solvent (H).

16. A dental primer comprising the polymerizable composition according to claim 8.

17. A dental bonding material comprising the polymerizable composition according to claim 8.

18. A dental cement comprising the polymerizable composition according to claim 8.

19. A dental composite resin comprising the polymerizable composition according to claim 8.

* * * * *